(12) United States Patent
Chelak et al.

(10) Patent No.: US 11,291,801 B2
(45) Date of Patent: Apr. 5, 2022

(54) PATIENT ACCESS SITE SECUREMENT SYSTEM

(71) Applicant: NP Medical, Inc., Clinton, MA (US)

(72) Inventors: Todd M. Chelak, Westborough, MA (US); Andrew Galanis, Marlborough, MA (US); Jonathan Gabel, Randolph, NJ (US)

(73) Assignee: NP Medical Inc., Clinton, MA (US)

( * ) Notice: Subject to any disclaimer, the term of this patent is extended or adjusted under 35 U.S.C. 154(b) by 0 days.

(21) Appl. No.: 16/778,477

(22) Filed: Jan. 31, 2020

(65) Prior Publication Data
US 2021/0236777 A1 Aug. 5, 2021

(51) Int. Cl.
*A61M 25/02* (2006.01)

(52) U.S. Cl.
CPC ..... *A61M 25/02* (2013.01); *A61M 2025/0246* (2013.01); *A61M 2025/0253* (2013.01); *A61M 2025/0266* (2013.01)

(58) Field of Classification Search
CPC .......... A61M 25/02; A61M 2025/0253; A61M 2025/0266; A61M 2025/0246; A61M 39/0247; A61M 39/22; A61M 39/10; A61M 39/105; A61M 2039/0258; A61M 2039/0261; A61M 25/0637; A61M 16/0683; A61M 16/0688; F16L 27/087; A61B 5/683; A61B 5/6833; A61B 5/6832; A61B 5/257; A61B 5/4236
See application file for complete search history.

(56) References Cited

U.S. PATENT DOCUMENTS

| 4,106,491 A | 8/1978 | Guerra |
| 4,123,091 A | 10/1978 | Cosentino et al. |
| 4,569,675 A | 2/1986 | Prosl et al. |
| 4,946,448 A | 8/1990 | Richmond |

(Continued)

FOREIGN PATENT DOCUMENTS

| EP | 422631 A1 | 4/1991 |
| JP | 2010-172763 A | 8/2010 |

(Continued)

OTHER PUBLICATIONS

International Search Report and Written Opinion for Application No. PCT/US2020/016140, dated Oct. 26, 2020.

*Primary Examiner* — Theodore J Stigell
*Assistant Examiner* — Rachel T. Smith
(74) *Attorney, Agent, or Firm* — McCarter & English LLP; Jonathan C. Lovely, Edq.

(57) ABSTRACT

A patient access site securement system includes a housing with an inlet, an outlet and an internal fluid path between the inlet and the outlet. The housing also has a connecting portion that connects to a catheter and/or a fluid line attached to the catheter. A contact surface is located on an underside of the housing and positions the patient access site securement system on the patient. A first reservoir with an interior holds a liquid and transitions from a first state to a second state. The interior is in fluid communication with the inlet when the reservoir is in the second state to allow the liquid to flow from the inlet, through the internal fluid path and exit the outlet. The liquid interacts with the contact surface and/or the patient to alter a level of securement between the catheter and the patient.

34 Claims, 17 Drawing Sheets

(56) References Cited

U.S. PATENT DOCUMENTS

| | | | |
|---|---|---|---|
| 5,139,483 A | 8/1992 | Ryan | |
| 5,205,834 A | 4/1993 | Moorehead et al. | |
| 5,259,835 A | 11/1993 | Clark et al. | |
| 5,354,282 A | 10/1994 | Bierman | |
| 5,693,025 A | 12/1997 | Stevens | |
| 5,707,348 A | 1/1998 | Krogh | |
| 5,865,808 A | 2/1999 | Corn | |
| 6,086,564 A | 7/2000 | McLaughlin | |
| 6,736,797 B1 | 5/2004 | Larsen et al. | |
| 7,413,561 B2 | 8/2008 | Raulerson et al. | |
| 8,585,655 B2 | 11/2013 | Bierman | |
| 8,790,311 B2 | 7/2014 | Gyrn | |
| 8,827,959 B2 | 9/2014 | Wright et al. | |
| 9,017,290 B2 | 4/2015 | Peters et al. | |
| 9,545,502 B2 | 1/2017 | Maseda et al. | |
| 9,642,987 B2 | 5/2017 | Bierman et al. | |
| 9,717,885 B1 | 8/2017 | Narciso Martinez et al. | |
| 9,827,398 B2 | 11/2017 | White et al. | |
| 11,013,902 B2 | 5/2021 | Chelak et al. | |
| 2006/0253086 A1* | 11/2006 | Moberg | A61M 5/1723 604/272 |
| 2006/0270994 A1 | 11/2006 | Bierman | |
| 2008/0269687 A1 | 10/2008 | Chong et al. | |
| 2010/0179481 A1 | 7/2010 | Bierman et al. | |
| 2010/0298777 A1 | 11/2010 | Nishtala | |
| 2011/0106014 A1 | 5/2011 | Helm, Jr. | |
| 2011/0257600 A1 | 10/2011 | Kessler | |
| 2011/0264058 A1* | 10/2011 | Linden | A61M 39/08 604/288.01 |
| 2012/0232490 A1 | 9/2012 | Andino | |
| 2012/0271240 A1 | 10/2012 | Andino et al. | |
| 2014/0276542 A1 | 9/2014 | Ciccone | |
| 2016/0317359 A1* | 11/2016 | Waller | A61M 39/0247 |
| 2018/0140821 A1 | 5/2018 | Purdy et al. | |
| 2019/0160275 A1 | 5/2019 | Funk et al. | |
| 2019/0275312 A1 | 9/2019 | Chelak et al. | |

FOREIGN PATENT DOCUMENTS

| | | | |
|---|---|---|---|
| WO | 2000/06230 A1 | 2/2000 | |
| WO | 2002/096494 A1 | 12/2002 | |
| WO | 2009/032008 A2 | 3/2009 | |
| WO | 2010/046893 A1 | 4/2010 | |
| WO | 2010/132837 A1 | 11/2010 | |
| WO | WO-2018206825 A1 * | 11/2018 | A61B 5/411 |

* cited by examiner

PATIENT ACCESS SITE SECUREMENT SYSTEM

TECHNICAL FIELD

The present invention relates to vascular access sites, and more particularly to devices and systems that care for a patient access site and utilize adhesives and/or other fluids that alter the level of securement to the patient.

BACKGROUND ART

In instances in which a patient will need regular administration of fluid or medications (or regular withdrawal of fluids/blood), catheters are often inserted into the patient and used to administer the fluids/medications. The catheter may remain in the patient for extended periods of time (several hours to several days or longer). Additionally, an extension tube may be connected to the catheter to facilitate use of the catheter and connection of a medical implement (e.g., a syringe). To ensure that the catheter and/or extension tube remain in place and are not accidentally removed, some prior art systems secure the catheter and/or extension tube to the patient using tape or similar adhesive materials (e.g., a film dressing).

Tapes and adhesive film dressings can be problematic in that they may not firmly secure the catheter in place, which can lead to local trauma to the vein and a medical condition referred to as phlebitis requiring removal of the catheter. Additionally, in some instances, the manner in which the tape is applied and the positioning/location of the catheter and/or extension tube may cause the catheter and/or extension tube to be bent. This, in turn, increases the risk of kinking (which can reduce/stop flow through the catheter and/or extension tube) and makes it more difficult to connect the medical implement required to introduce the fluid/medication. In devices that utilize adhesives, there may not be sufficient adhesive to secure the device/catheter for the duration of treatment and in other instances it may be difficult to remove the adhesive and device from the patient potentially leading to skin injury. Furthermore, the deployment of these adhesive-based securement devices can be cumbersome for the user as they attempt to remove release liners and blindly position an underside upon the patient (which can contribute to improper adherence to the body and poor securement performance).

SUMMARY OF THE INVENTION

In accordance with one embodiment of the invention, a patient access site securement system for securing a patient line to a patient may include a housing, a contact surface on the underside of the housing, and a first reservoir. The housing may have a first inlet, a first outlet and an internal fluid path between the first inlet and the first outlet. The housing may also have a connecting portion that may connect to a catheter and/or a fluid line attached to the catheter. The contact surface may position the patient access site securement system on the patient. The first reservoir has an interior that holds a first liquid, and may transition from a first state to a second state. The interior may be in fluid communication with the first inlet when the reservoir is in the second state to allow the first liquid to flow from the first inlet, through the internal fluid path and exit the first outlet such that the first liquid interacts with the contact surface and/or the patient to alter a level of securement between the catheter and the patient. The first liquid may be an adhesive that increases the level of securement between the catheter and the patient after interacting with the contact surface and/or the patient. Alternatively, the first liquid may be an adhesive remover that decreases the level of securement between the catheter and the patient after interacting with the contact surface and/or the patient.

In some embodiments, at least a portion of the first reservoir may move relative to the first inlet from a first position to a second position to transition the first reservoir from the first state to the second state. Additionally or alternatively, the housing may include a second inlet, a second outlet and a second internal fluid path between the second inlet and second outlet. In such embodiments, the system may also have a second reservoir with a second reservoir interior that holds a second liquid. The second reservoir may also transition from a first state to a second state. The second reservoir interior may be in fluid communication with the second inlet when the second reservoir is in the second state to allow the second liquid to flow from the second inlet, through the second internal fluid path and exit the second outlet. The second liquid may interact with the contact surface, the first liquid, and/or patient to alter a level of securement between the catheter and the patient.

The housing may also include at least one access element that may breach a portion of the first reservoir when transitioning towards the second state to allow the first fluid to flow into the first inlet. For example, the first reservoir may have a breachable portion, and the access element(s) may breach the breachable portion. The access element may, at least partially, enter the interior of the first reservoir when in the second state to displace at least a portion of the first liquid within the interior. The access element may be a cutting element. The first reservoir may be removable from the patient access site securement system. Some portion of the first liquid may also interact with the catheter insertion site after exiting the first outlet such as to seal the site opening.

In other embodiments, the contact surface may include an adhering layer that secures the patient access site securement system to the patient. Additionally or alternatively, the contact surface may include at least one fluid channel and/or at least one wicking member to facilitate fluid dispersion from the first outlet. The volume within the first reservoir may be reduced as the reservoir transitions from the first state to the second state. The system may also include a protective cap that is removeably secured to the system and covers a portion of the first reservoir. The protective cap may prevent the reservoir from transitioning from the first state to the second state when secured to the patient access site securement system. The connecting portion may have a first protrusion and optionally a second protrusion (e.g., that may form a C-clamp) that extends from a surface of the housing to receive and secure the fluid line and/or catheter. At least the first protrusion may flex while receiving the catheter and/or fluid line.

In accordance with further embodiments, a method for securing a patient line to a patient includes providing a patient access site securement system that includes a housing with a first inlet, a first outlet and an internal fluid path between the first inlet and the first outlet. The housing may also have a connecting portion that may connect to the catheter and/or a fluid line attached to the catheter. A contact surface may be located on an underside of the housing and may position the patient access site securement system on the patient. A first reservoir may have an interior configured to hold a first liquid and may transition from a first state to a second state. The interior may be in fluid communication with the first inlet when the reservoir is in the second state to allow the first liquid to flow from the first inlet, through the internal fluid path and exit the first outlet. The method may also include positioning the contact surface on the patient, connecting the catheter and/or a fluid line to the connecting portion of the housing, and transitioning the first reservoir from the first state to the second state. This, in turn, causes the first fluid to interact with the contact surface and/or the patient and alter a level of securement between the catheter and the patient.

In accordance with some embodiments, the first liquid may be an adhesive that increases the level of securement between the catheter and the patient after interacting with the contact surface and/or the patient. Alternatively, the first liquid may be an adhesive remover that decreases the level of securement between the catheter and the patient after interacting with the contact surface and/or the patient. In some embodiments, transitioning the first reservoir from the first state to the second state may include moving at least a portion of the first reservoir relative to the first inlet and from a first position to a second position.

The housing may have a second inlet, a second outlet and a second internal fluid path between the second inlet and second outlet. In such embodiments, the patient access site securement system may include a second reservoir having a second reservoir interior that holds a second liquid. The method may then transition the second reservoir from a first state to a second state in which the second reservoir interior is in fluid communication with the second inlet. This, in turn, allows the second liquid to flow from the second inlet, through the second internal fluid path and exit the second outlet such that the second liquid interacts with the contact surface, the first liquid, and/or patient to alter a level of securement between the catheter and the patient.

The housing may include an access element that breaches at least a portion of the first reservoir when transitioning towards the second state to allow the first fluid to flow into the first inlet. The first reservoir may have a breachable portion, and the access element may breach the breachable portion and/or at least partially enter the interior of the first reservoir when in the second state to displace at least a portion of the first liquid within the interior. In some embodiments, the access element may be a cutting element. The first reservoir may be configured to be removed from the patient access site securement system and/or at least a portion of the first fluid may interact with a catheter insertion site after exiting the first outlet.

In additional embodiments, the contact surface may have an adhering layer that secures the patient access site securement system to the patient. Additionally or alternatively, the contact surface includes one or more fluid channels and/or at least one wicking member that facilitate fluid dispersion from the first outlet. The patient access site securement system may also include a protective cap that may be removeably secured to the patient access site securement system and may cover the first reservoir. The protective cap may prevent the reservoir from transitioning from the first state to the second state when secured to the patient access site securement system. In some embodiments, the connecting portion may include a first protrusion and optionally a second protrusion that extends from a surface of the housing. At least the first protrusion may flex to receive and secure the fluid line and/or partly form a c-clamp that receives and secures the fluid line.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a patient access site securement system includes a housing with a contact surface on the underside and a reservoir. The contact surface may position the patient access site securement system on the patient. The housing may also have a connecting portion that may connect to a catheter and/or a fluid line attached to the catheter. The reservoir may hold a liquid and may transition from a first state to a second state in which the interior of the reservoir is in fluid communication with an inlet in the housing. When in the second state, the fluid may exit the reservoir, flow into the inlet of the housing, through an internal fluid path within the housing and exit an outlet where the liquid interacts with the contact surface and/or a patient to alter a level of securement (e.g., increase securement or decrease securement) between the catheter and the patient.

Figure 1:
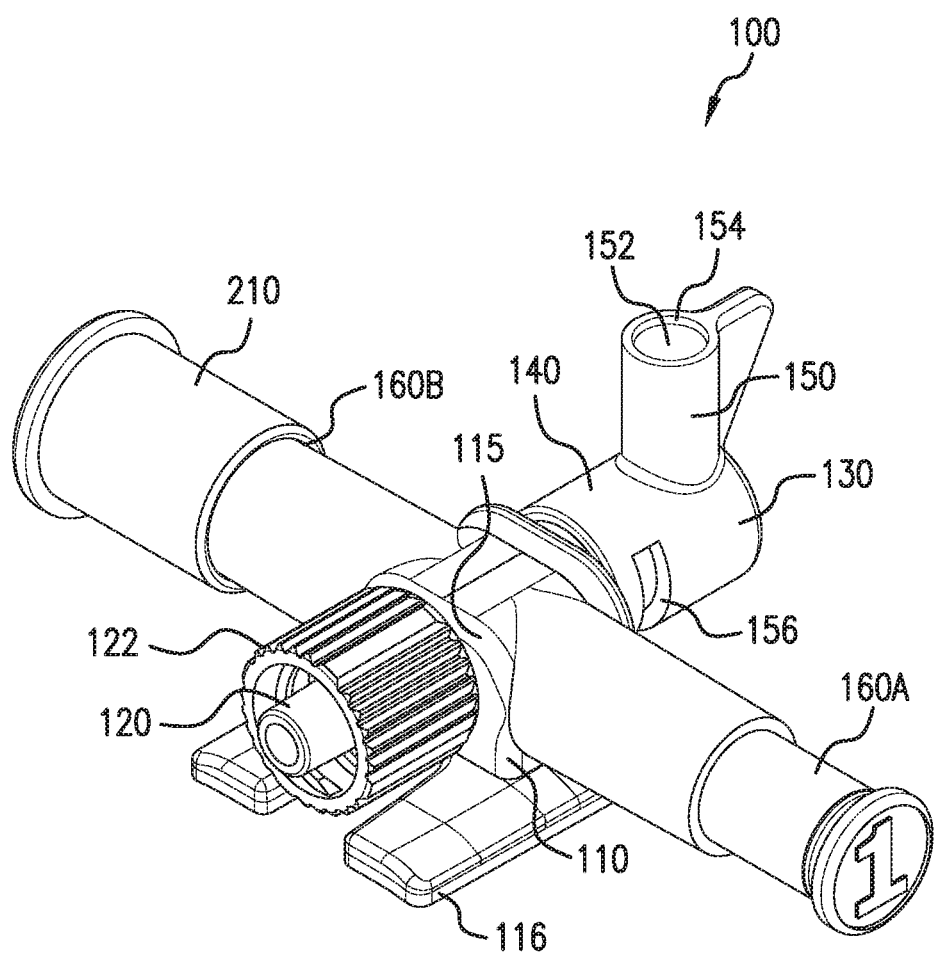
FIG. 1 schematically shows a perspective view of a patient access site securement system in a pre-activated state, in accordance with some embodiments of the present invention.
Figure 2:
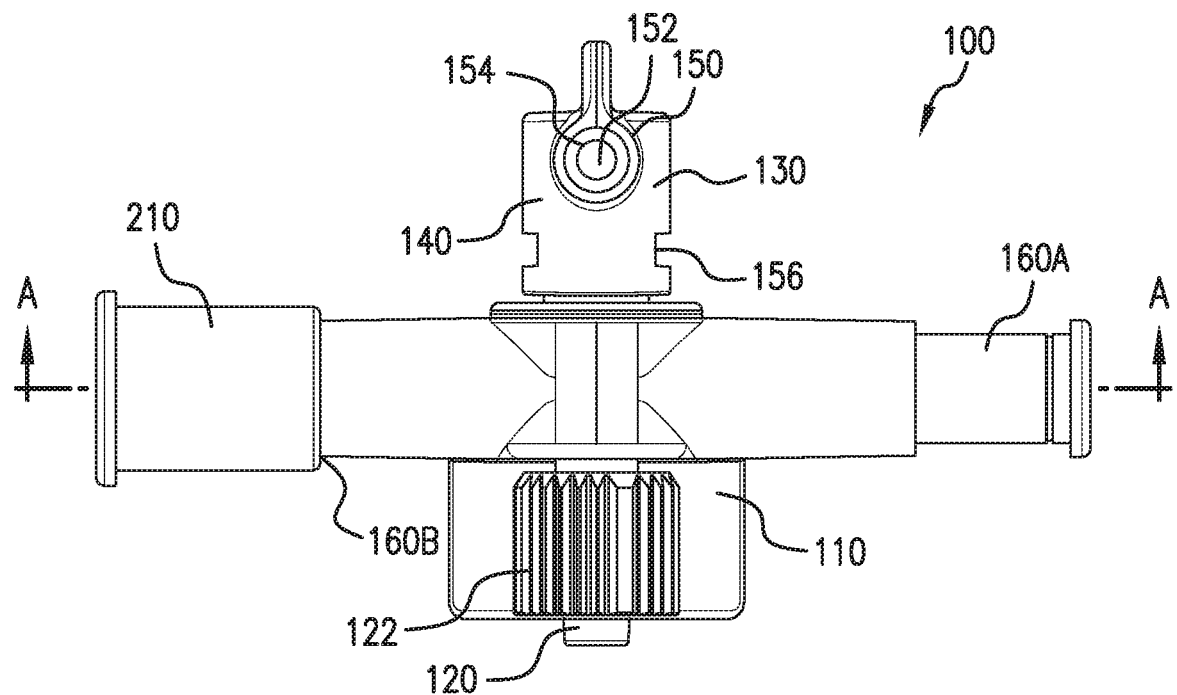
FIG. 2 schematically shows a top view of the patient access site securement system shown in FIG. 1, in accordance with various embodiments of the present invention.
Figure 3:
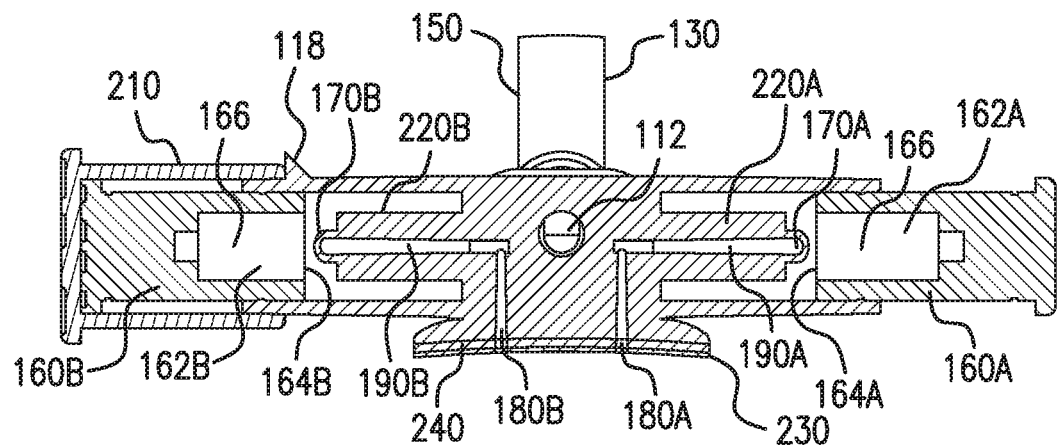
FIG. 3 schematically shows a cross-sectional view of the patient access site securement system shown in FIG. 1, in accordance with some embodiments of the present invention.
Figure 4:
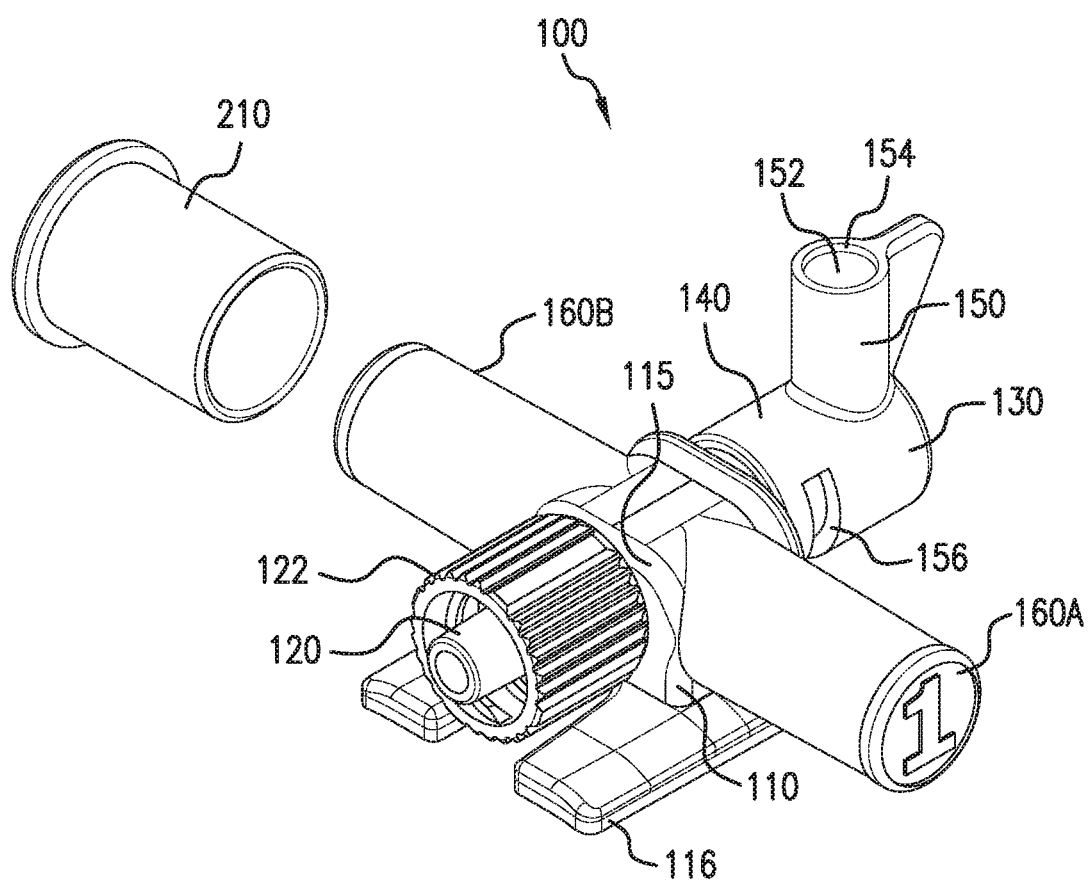
FIG. 4 schematically shows a perspective view of the patient access site securement system shown in FIG. 1 in the post-activation state, in accordance with various embodiments of the present invention.
Figure 5:
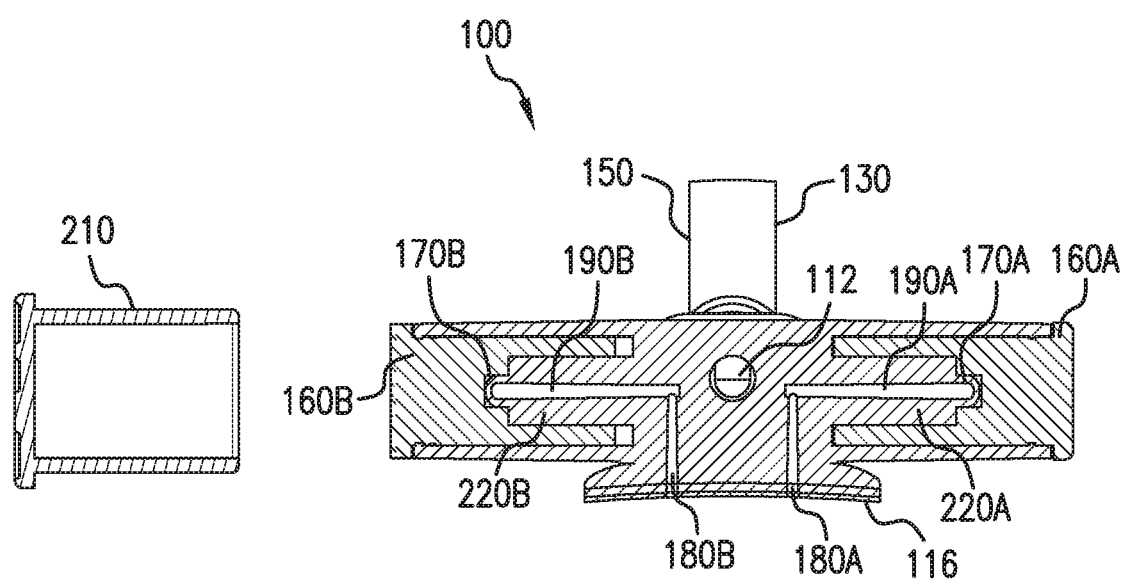
FIG. 5 schematically shows a cross-sectional view of the patient access site securement system shown in FIG. 1 in the post-activation state, in accordance with some embodiments of the present invention.

FIGS. 1-2 and 4 schematically show a patient access site securement system 100 in both a pre-activation state (FIGS. 1-2) and a post-activation state (FIG. 4), in accordance with some embodiments of the present invention. FIGS. 3 and 5 schematically show cross-sectional views of the patient access site securement system 100 in the pre-activation state (FIG. 3) and the post-activation state (FIG. 5). The system 100 may have a housing 110 with a contact surface 116 located on the underside, and a connecting portion 115 that may connect to the catheter and/or a fluid line attached to the catheter. For example, the connecting portion 115 may include a male luer connector 120 extending from one side of the housing 110 and a rotatable flow housing 130 extending from the other. During use, the male luer connector 120 may connect to a catheter (not shown) that has been introduced into the patient. The system 100 may include a locking mechanism (e.g., a threaded ring 122, locking arms, etc.) for securing the male luer connector 120 to the catheter.

The flow housing 130 may have a sleeve portion 140 and a pathway portion 150 extending from the sleeve portion 140. As the name suggests, the pathway portion 150 may include a flow path 152 that extends through it and that is fluidly connected to a flow path 112 within the housing 110 (see FIG. 3) to allow an IV therapy fluid and/or blood to pass through the device 100. The inlet 154 of the flow path 152 may connect directly to a medical implement used to transfer fluid to and/or from the patient through the device 100. Alternatively, the device 100 may include a tube (not shown) that is connected to the inlet 154 of the flow path 152. In such embodiments, the tube may have or may be connected to a medical connector (e.g., a female luer connector), a needle free connector (not shown) or other medical device such as a luer activated valve (not shown) at the other end.

The flow housing 130 may be rotatably connected to the housing 110 such that flow housing 130 can rotate between a left-facing position (e.g., such that the inlet 154 is facing to the left), a right-facing position (e.g., such that the inlet 154 is facing to the right), and a upward-facing position (e.g., such that the inlet 154 is facing upwards, for example, as shown in FIG. 1). To that end, the housing 110 may have a protrusion extending from a surface of the housing 110. Conversely, the flow housing 130 (e.g., the sleeve portion 150) may include a recess 156 into which the protrusion may snap during assembly of the device 100.

Extending from one or more sides of the housing 110, the system/device 100 may have one or more reservoirs 160A/B with an interior 162A/B that contains a liquid that may alter the level of securement between the patient and the system/device 100. For example, the reservoirs 160A/B may contain an adhesive (e.g., a cyanoacrylate or similar adhesive) that can be used to secure the device 100 and/or catheter to the patient (e.g., increase the level of securement), and/or an adhesive remover that may be used to help remove the device 100/catheter from the patient (e.g., reduce the level of securement). Alternatively, one reservoir 160A may contain an adhesive and the other reservoir 160B may contain the remover. As discussed in greater detail below, the reservoirs 160A/B may transition between a first/pre-activated state to a second/post-activated state to allow the fluid 166 within the reservoirs 160A/B to interact with the contact surface 116 of the housing 110 and/or the patient to alter the level of securement.

To prevent the accidental transition of the reservoirs 160A/B to the post-activated state, the system/device 100 may include a cap 210 that may be placed over each of the reservoirs 160A/B and secured to the housing 110. For example, the cap 210 may have a protrusion that extends into a recess within the housing 110 and/or the housing 100 may include a protrusion that extends into a recess on the cap 210. The cap 210 may be removed prior to use to allow the user to actuate/transition the reservoirs 160A/B. Additionally, to prevent the cap from being depressed and accidentally transitioning the reservoirs 160A/B, the system/device 100 may include a stop 118 extending from a portion of the housing 110 and against which the end of the cap 210 contacts when in place over the reservoir 160A/B.

To facilitate the transfer of the fluid 166 from the interior 162A/B of the reservoir 160A/B to the contact surface 116 and/or the patient, the housing 110 may have one or more inlets 170A/B, one or more outlets 180A/B, and one or more internal fluid paths 190A/B connecting the inlets 170A/B and outlets 180A/B. For example, the housing 110 may include one inlet 170A/B, one outlet 180A/B, and one internal fluid path 190A/B for each reservoir 160A/B. Alternatively, as discussed in greater detail below, there may be multiple inlets, outlets and internal fluid paths for each reservoir. Additionally, in order to access the interior 162A/B of each of the reservoirs 160A/B, the housing 110 may also include an access element 220A/B (e.g., a piston like structure) for each of the reservoirs 160A/B. As discussed in greater detail below, the access element 220A/B may be configured to breach a portion of the associated reservoir 160A/B (e.g., it may breach a breachable portion 164A/B) and enter the reservoir 160A/B to displace at least a portion of the fluid 166 within the interior 162A/B. The breachable portion 164A/B may be foil or plastic film/ membrane that covers one end (e.g., an open end) of the reservoir 160A/B and may easily break/breach (e.g. be cut) when the access element 220A/B applies pressure to the film.

During use, the user may place the system/device 100 on the patient such that the contact surface 116 of the housing 110 positions the device 100 on the patient and then connect the catheter and/or the fluid line to the connecting portion 115 of the device 100. Alternatively, the user may first connect the system 100 to the catheter and/or fluid line and then place the system 100 on the patient. If one or more of the reservoirs 160A/B contains an adhesive to be used to secure the system/device 100 to the patient, the user may remove the cap 210 (if equipped) and then depress the reservoir that contains the adhesive (e.g., reservoir 160A) to move the reservoir 160A relative to the inlet 170A. As the reservoir 160A transitions from the first/pre-activated state toward the second/post-activated state, the access member 220A will breach the breachable portion 164A of the reservoir 160A and begin to enter the interior 162A of the reservoir 160A, displacing at least a portion of the fluid/adhesive within the reservoir 160A. The fluid 166 will then enter the inlet 170A, flow through the internal fluid path 180A and contact/interact with the contact surface 116 and/or the patient's skin to secure the system/device 100 to the patient (e.g., to increase the level of securement of the device 100). Depending on the type of adhesive used, the user may also expose the adhesive to UV light or perform other additional steps to help cure the adhesive.

Conversely, if the reservoir (e.g., reservoir 160B) contains an adhesive remover (e.g., if the contact surface 116 has its own adhesive layer to secure the system/device 100 to the patient) or the patient has completed IV therapy or other treatment and the user is now removing the device 100 from the patient, the user may remove the cap on reservoir 160B (if equipped) and depress the reservoir that contains the remover (e.g., reservoir 160B) to move the reservoir 160B relative to the inlet 170B. As the reservoir 160B transitions from the first/pre-activated state toward the second/post-activated state, the access member 220B will breach the breachable portion 164B of the reservoir 160B and begin to enter the interior 162B of the reservoir 160B, displacing at least a portion of the fluid/adhesive remover within the reservoir 160B. The fluid 166 will then enter the inlet 170B, flow through the internal fluid path 180B and contact/interact with the contact surface 116 and/or the patient's skin to dissolve/weaken the adhesive and allow the system/device 100 to be removed from the patient (e.g., to decrease the level of securement of the device 100).

It should be noted that, although FIGS. 1-5 show a system 100 with two reservoirs 160A/B and is described above as having a reservoir 160A with adhesive and another reservoir 160B with adhesive remover, other embodiments may have only a single reservoir containing either adhesive or adhesive remover. Alternatively, the system 100 may have more than two reservoirs 160A/B containing various combinations of fluids (e.g., all containing adhesive, all containing remover, and/or some containing adhesive and some containing remover). Additionally, in other embodiments, the reservoirs 160A/B may contain fluids other than adhesive and/or adhesive remover. For example, the reservoirs 160A/B may contain a cleaning fluid, an antiseptic fluid, etc. Alternatively or in addition, the one or more internal fluid paths 190A/B may contain a substance (e.g. adhesive powder) that interacts with the fluid 166 while passing therethrough, the mixture then altering the level of securement between the patient and the system/device 100.

To ensure that the fluid 166 (e.g., the adhesive, adhesive remover, or other fluid) is thoroughly and/or evenly dispersed across the contact surface 116, the housing 110 may include a number of components and structures that allows the fluid 166 to flow across the contact surface 116. For example, the underside of the contact surface 116 may have a number of channels (e.g. grooves, texturing, and/or similar features) into which the fluid 166 enters as it exits the outlets 180A/B and in which the fluid 166 may flow across the contact surface 116 and/or the patient's skin. Additionally or alternatively, the housing 110 may include one or more material layer 230 that helps to disperse the fluid 166. The material layer 230 may include wicking material, hydrophilic material and/or an absorbent material into which the fluid 166 (e.g. adhesive) absorbs. In such embodiments, the device 100 may also include a release layer 240 located above the wicking/absorbent layer 230 and the adhesive remover may exit the outlet 180B onto this release layer 240 to release the device 100 from the wicking/absorbent layer 230.

Figure 8A:
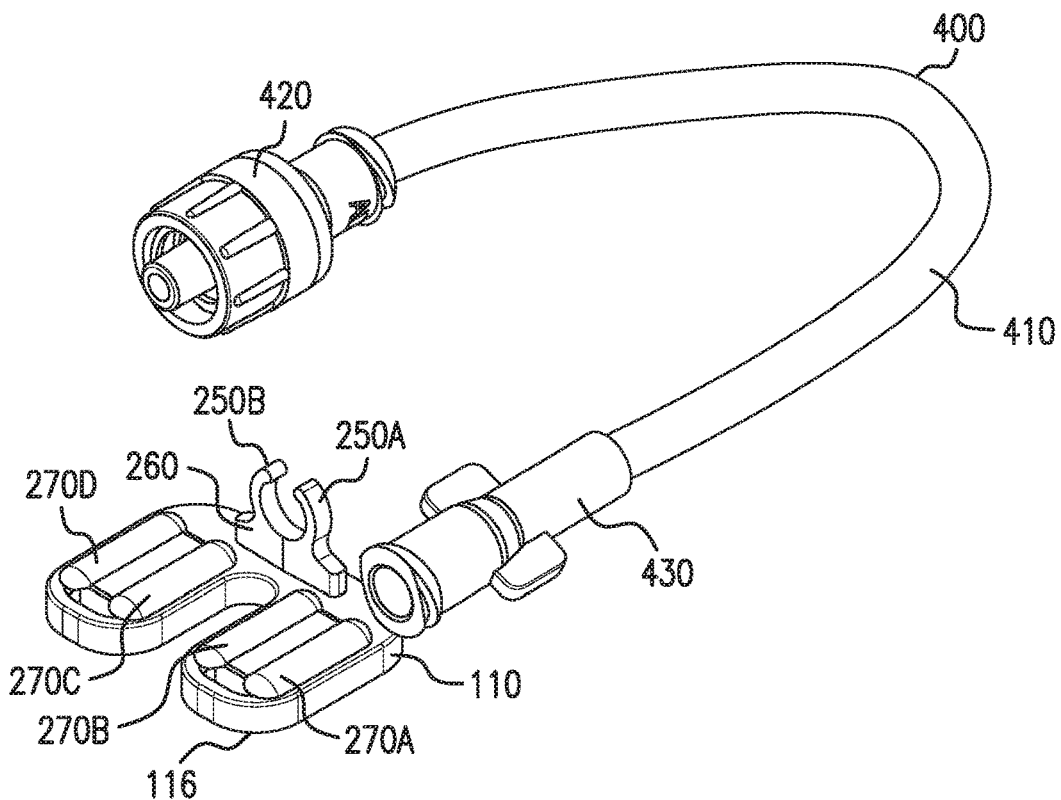
FIGS. 8A and 8B schematically show the patient access site securement system shown in FIG. 6 with a fluid line (e.g., a tubing set) unconnected and connected, in accordance with various embodiments of the present invention FIGS. 9A and 9B schematically shows a cross-sectional view and a detail view of the patient access site securement system shown in FIG. 6, in accordance with some embodiments of the present invention.
Figure 8B:
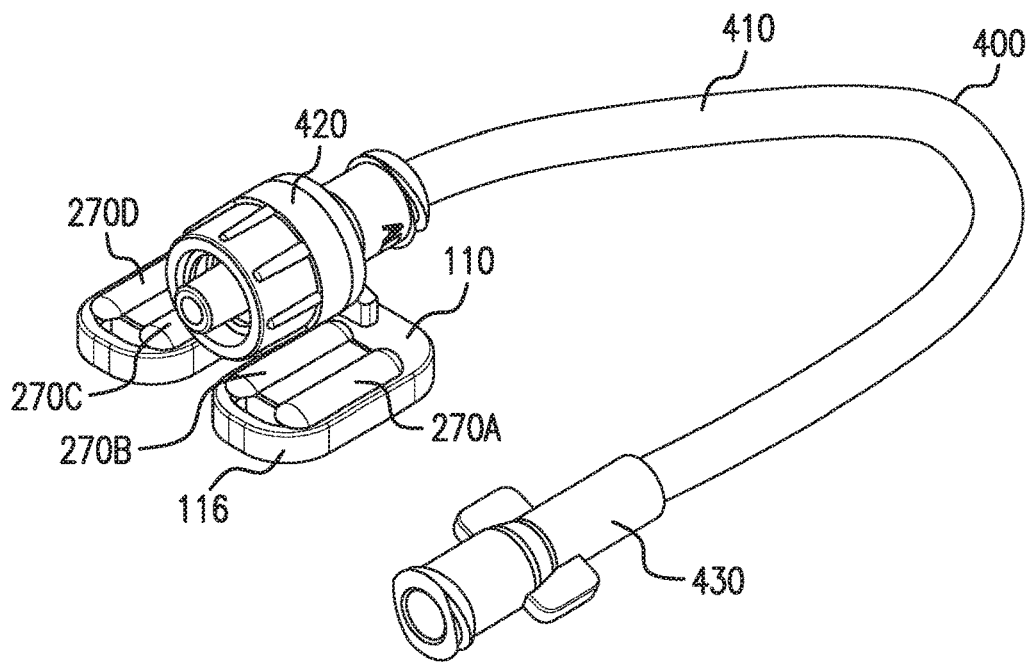
Figure 9A:
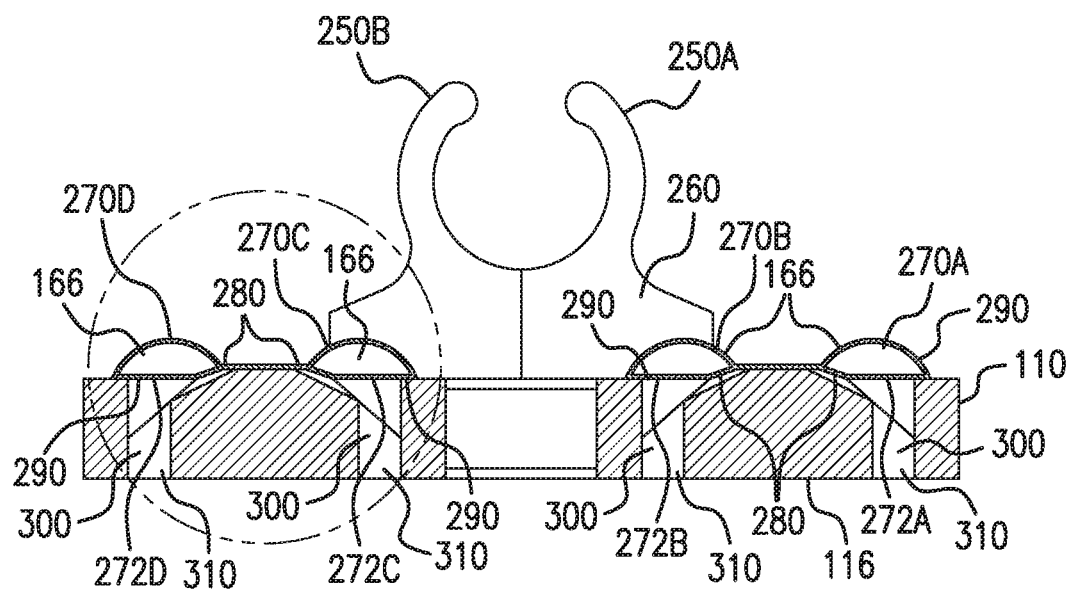
Figure 9B:
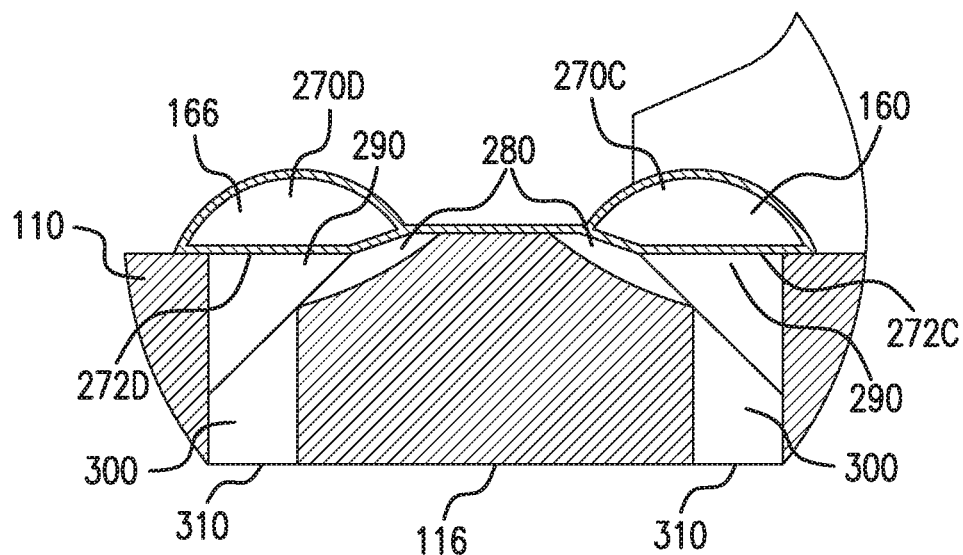
Figure 10A:
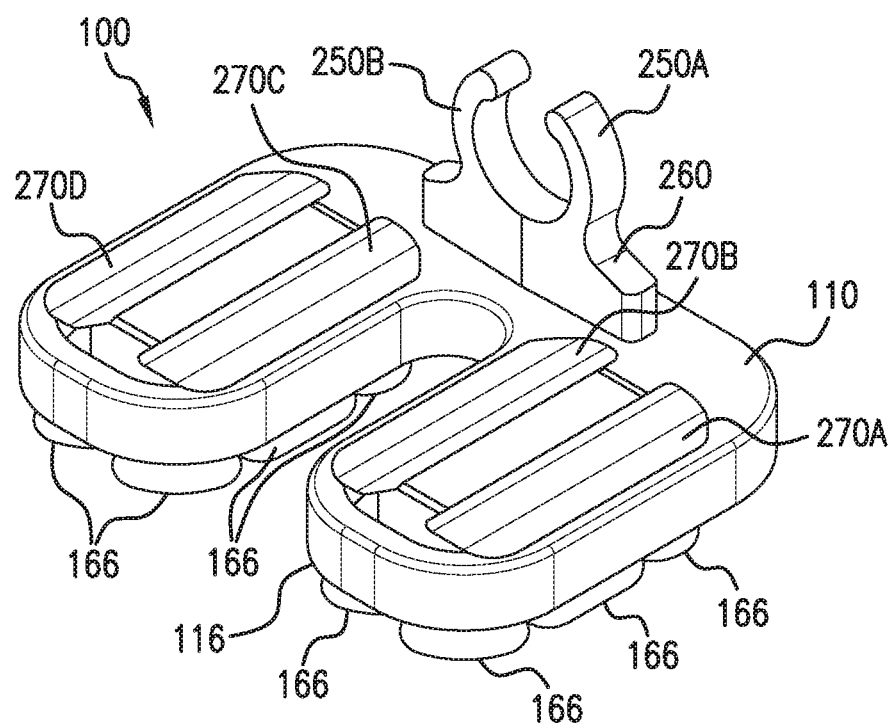
FIGS. 10A and 10B schematically shows a perspective view and a top view of the patient access site securement system shown in FIG. 6 in the post-activation state, in accordance with various embodiments of the present invention.
Figure 10B:
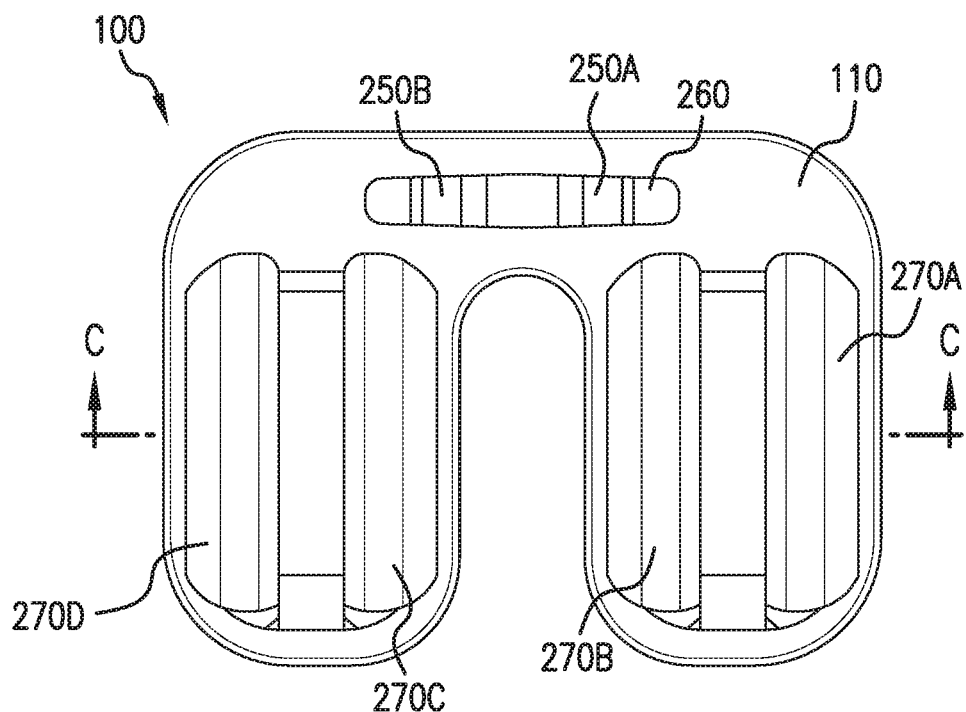
Figure 11A:
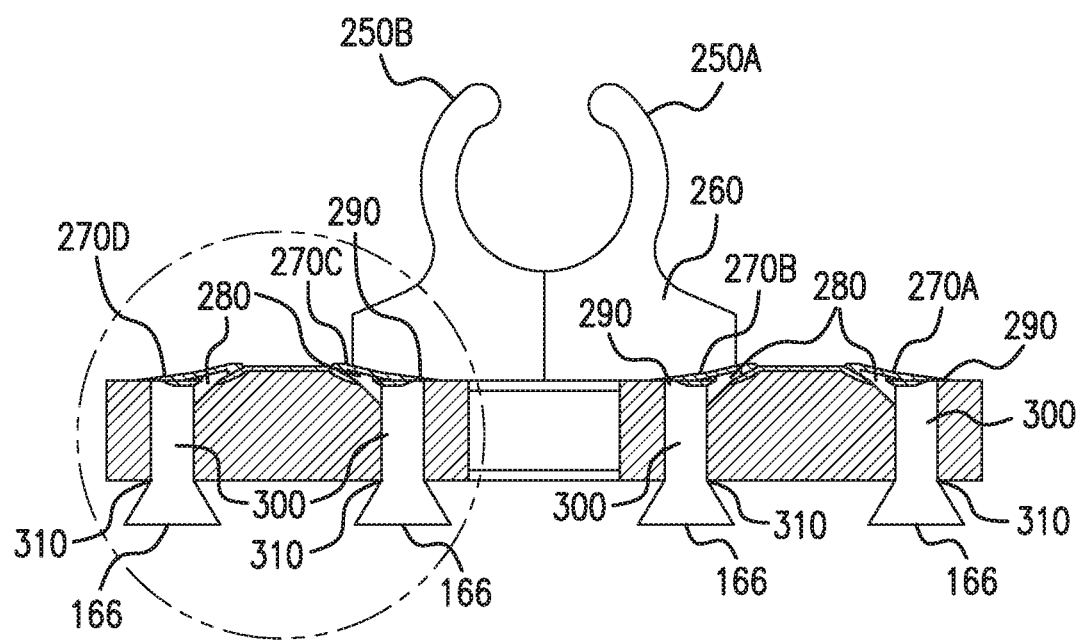
FIGS. 11A and 11B schematically shows a cross-sectional view and a detail view of the patient access site securement system shown in FIG. 6 in the post-activation state, in accordance with some embodiments of the present invention.
Figure 11B:
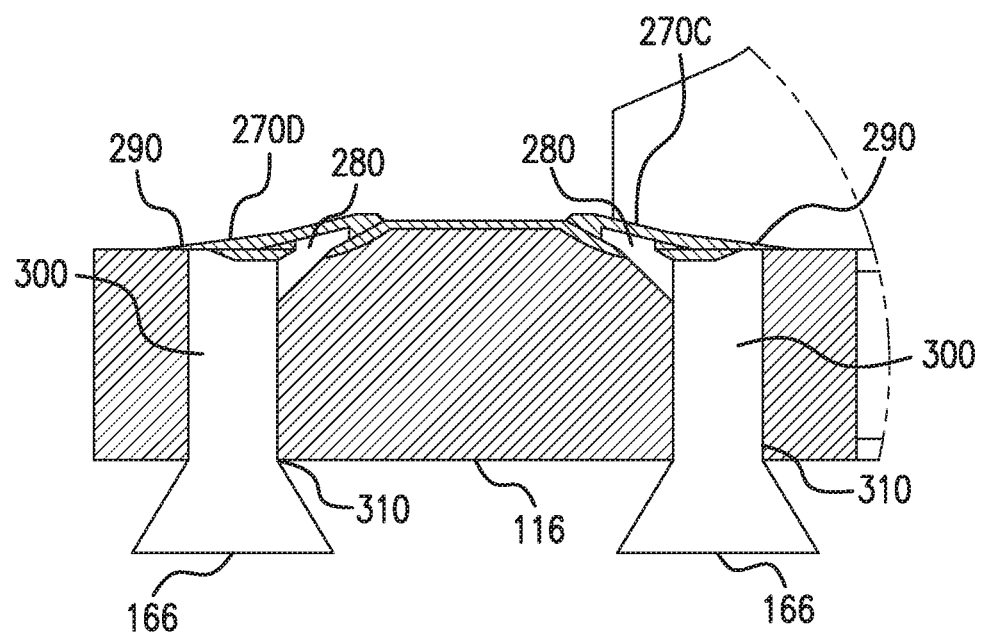
Figure 12:
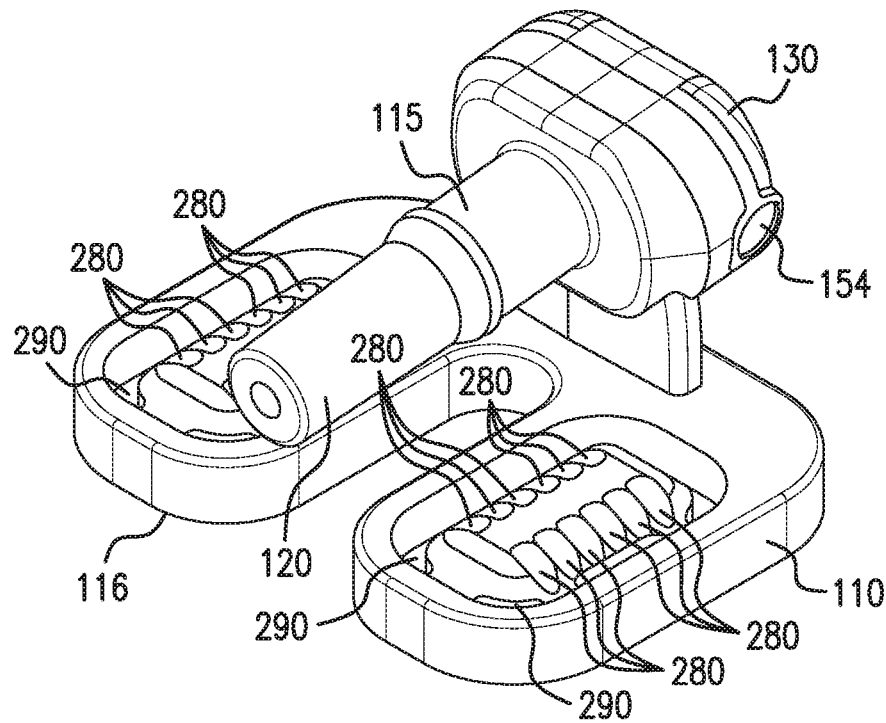
FIG. 12 schematically shows a perspective view of an additional embodiment of a patient access site securement system with reservoirs removed, in accordance with some embodiments of the present invention.
Figure 13A:
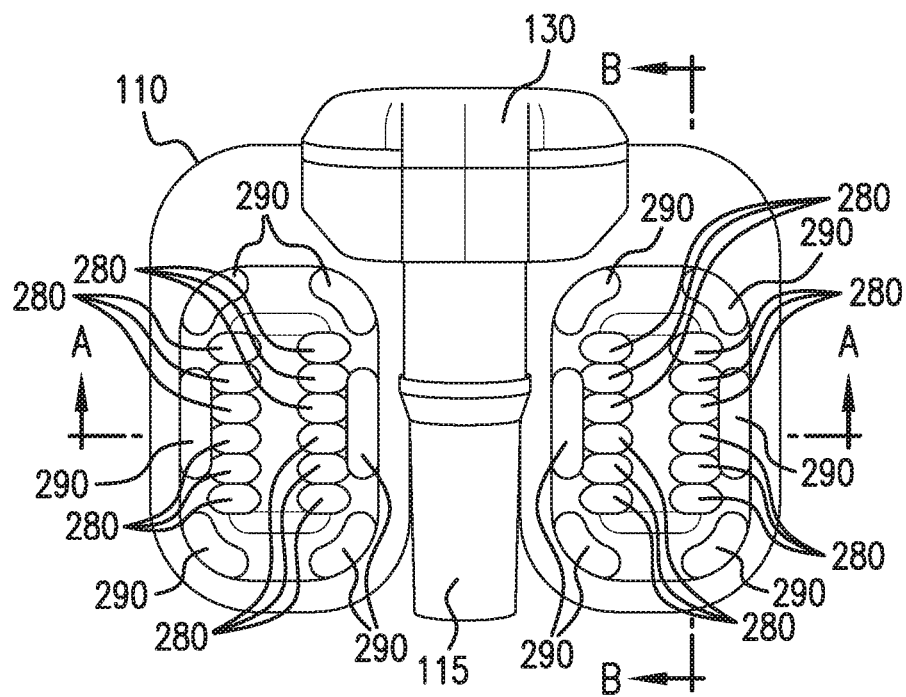
FIG. 13A schematically shows a top view of the patient access site securement system shown in FIG. 12, in accordance with various embodiments of the present invention.
Figure 13B:
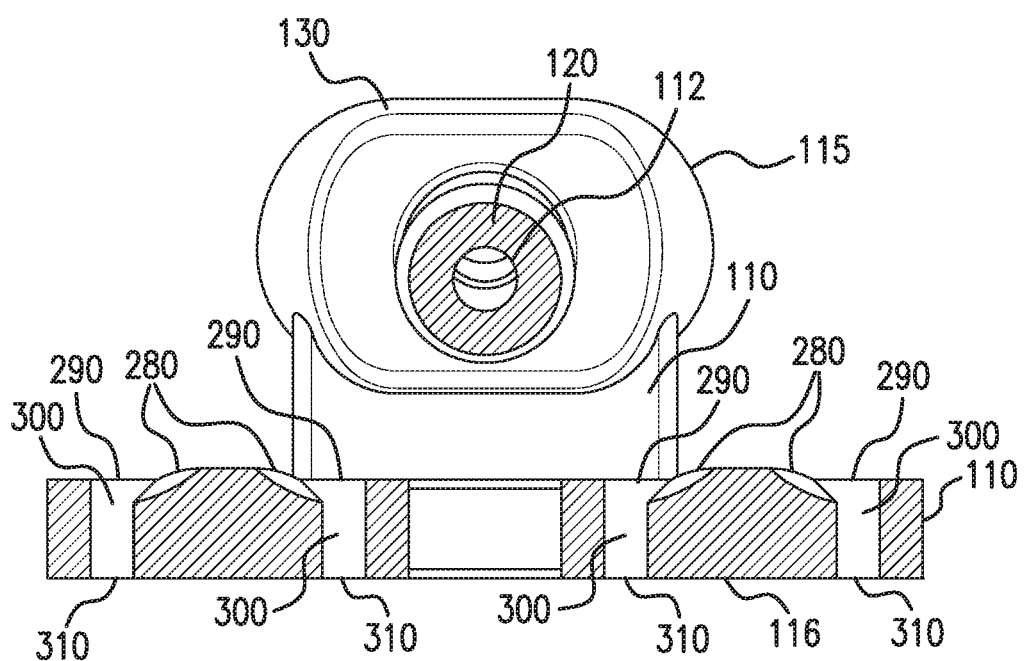
FIGS. 13B and 13C schematically shows cross-sectional views of the patient access site securement system shown in FIG. 12, in accordance with some embodiments of the present invention.
Figure 13C:
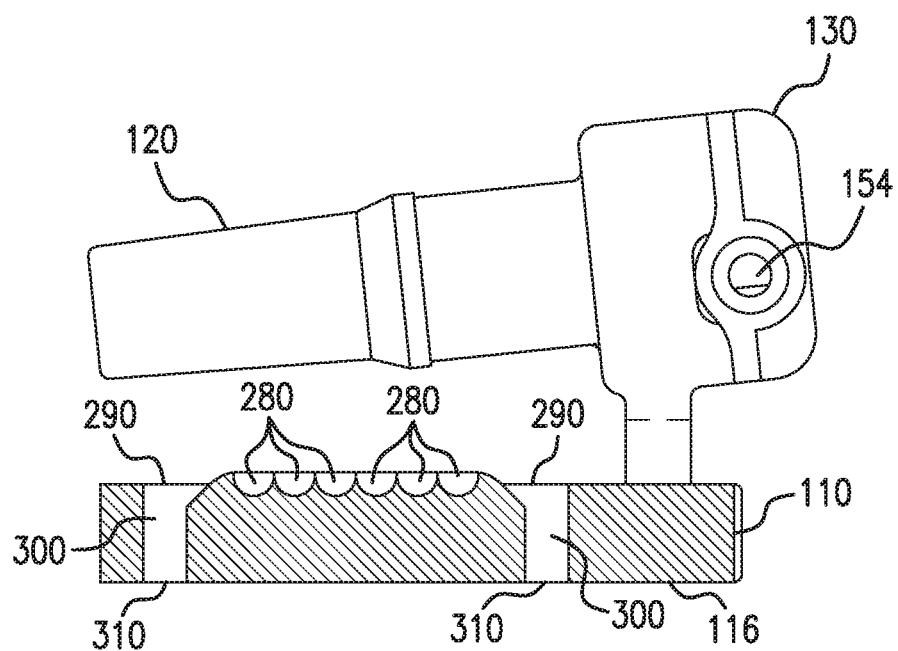
Figure 14A:
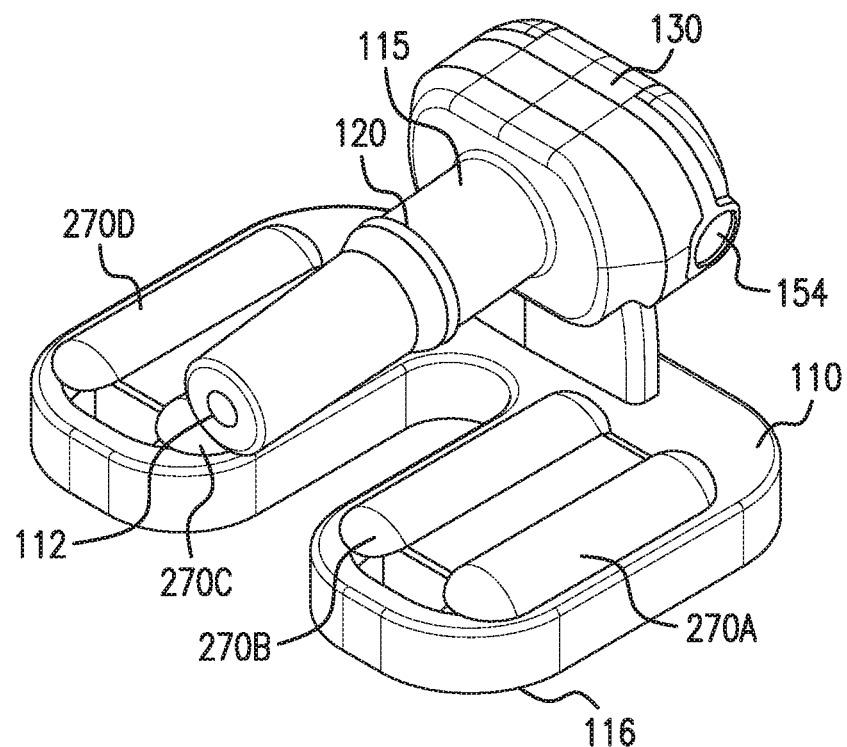
FIGS. 14A and 14B schematically show a perspective view and a top view of the patient access site securement system shown in FIG. 12 in the pre-activation state with the reservoirs in place, in accordance with various embodiments of the present invention.
Figure 14B:
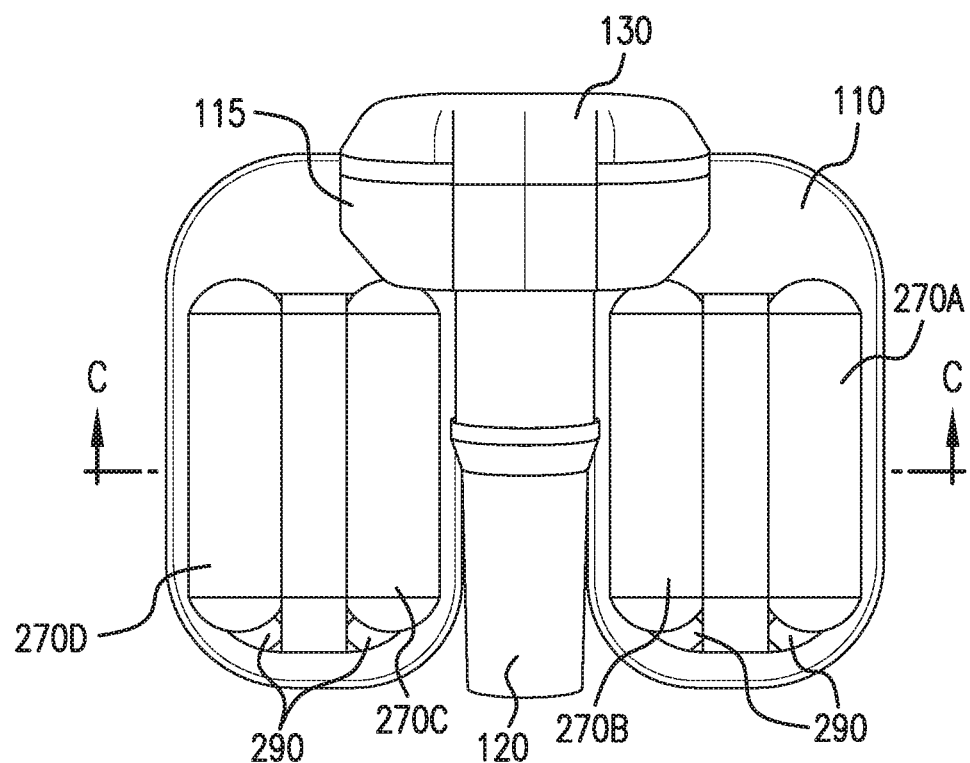
Figure 14C:
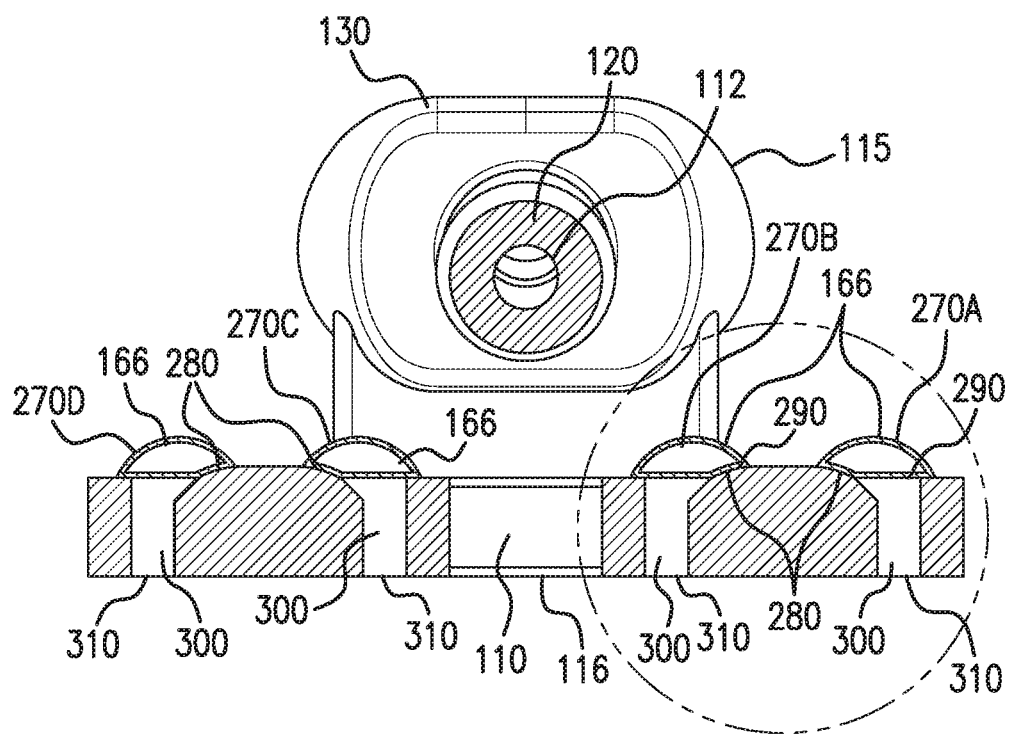
FIGS. 14C and 14D schematically shows a cross-sectional view and a detail view of the patient access site securement system shown in FIG. 12 in the pre-activation state with the reservoirs in place, in accordance with some embodiments of the present invention.
Figure 14D:
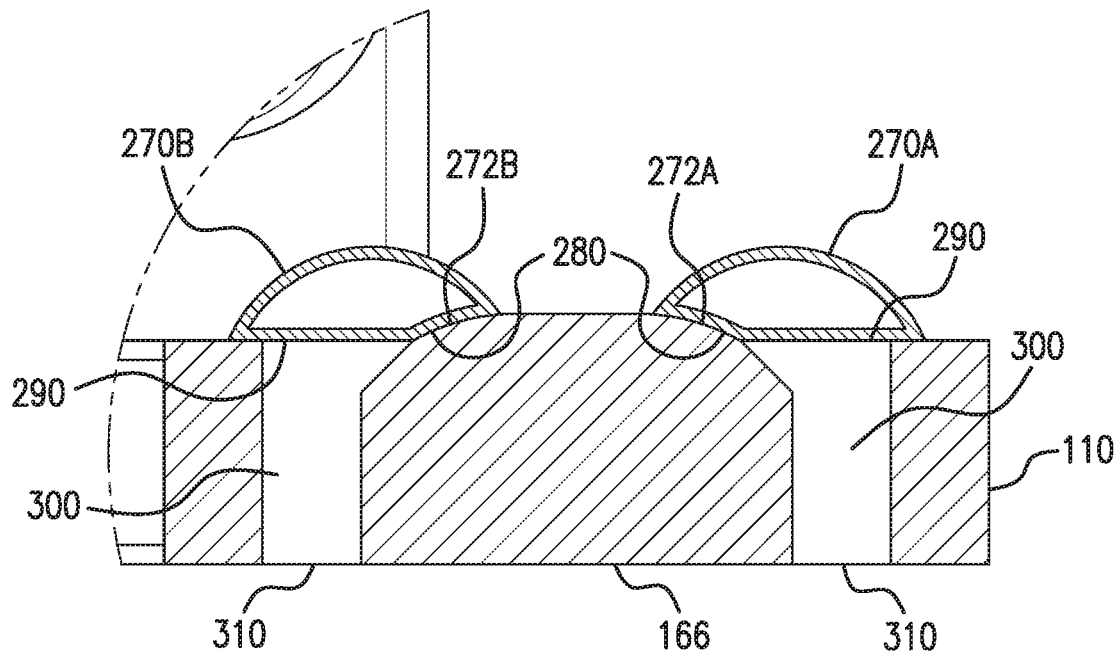
Figure 15A:
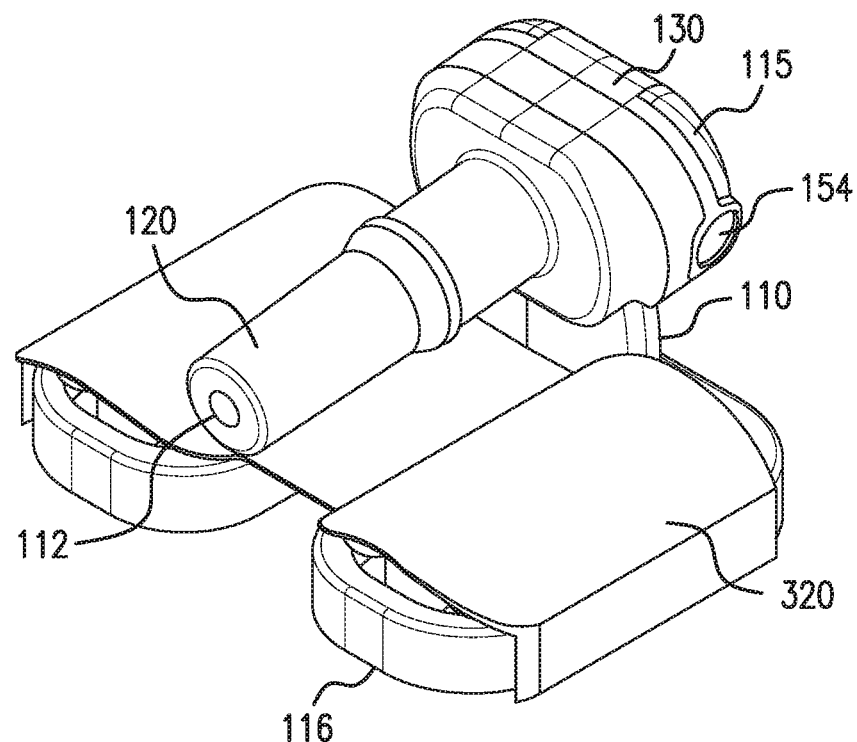
FIGS. 15A to 15C schematically shows various views of the patient access site securement system shown in FIG. 12 with a protective cover in place, in accordance with some embodiments of the present invention.
Figure 15B:
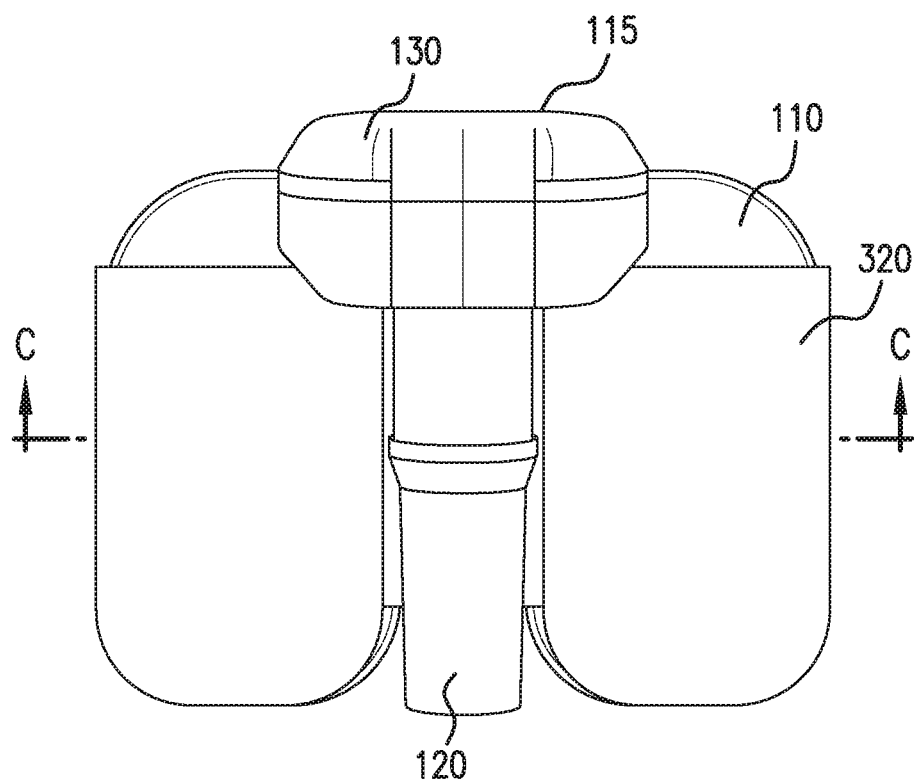
Figure 15C:
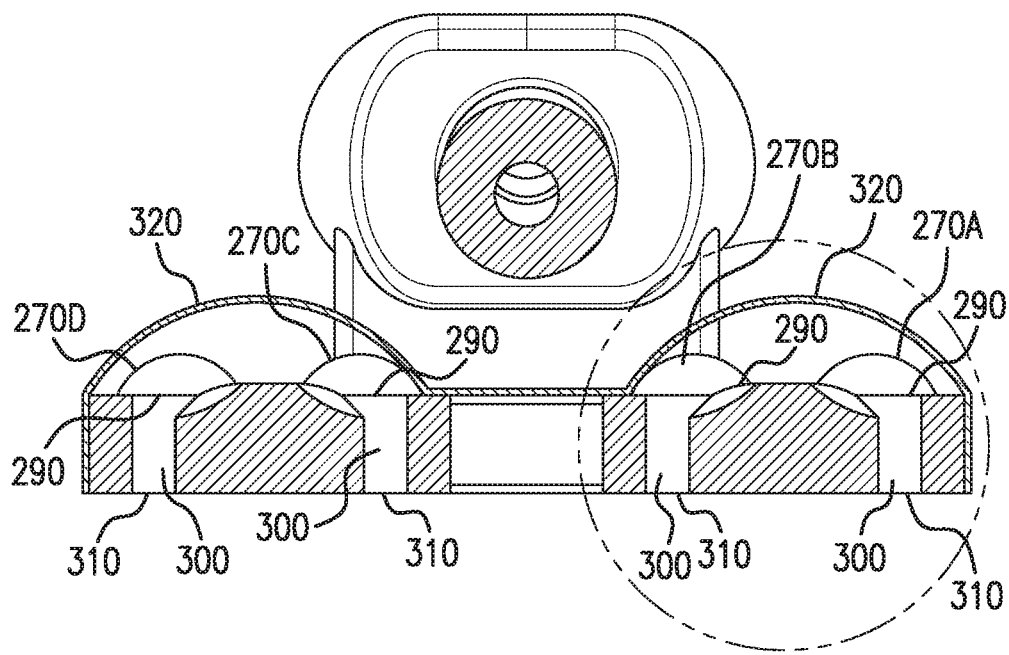
Figure 16A:
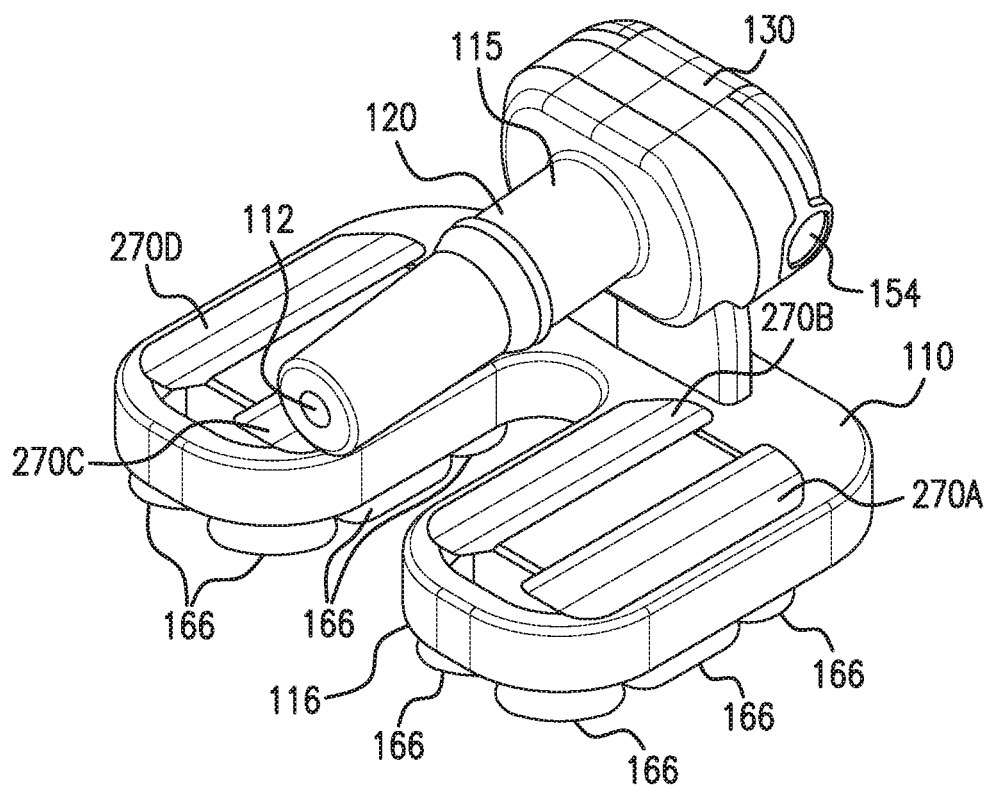
FIGS. 16A to 16C schematically shows various views of the patient access site securement system shown in FIG. 12 in the post-activated state, in accordance with some embodiments of the present invention.
Figure 16B:
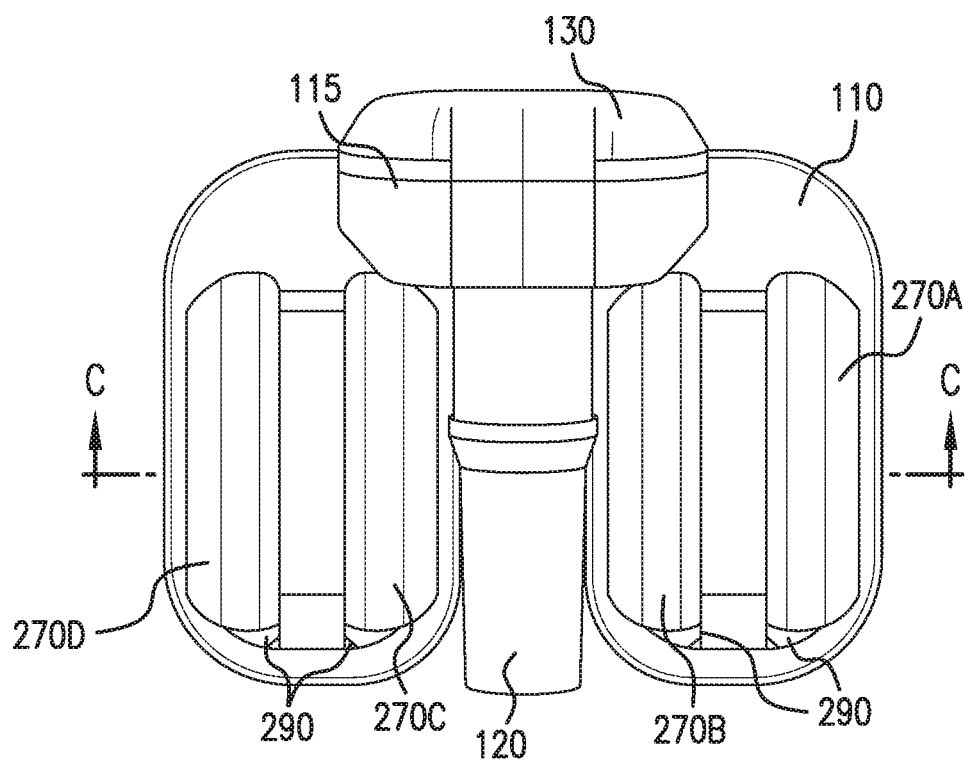
Figure 16C:
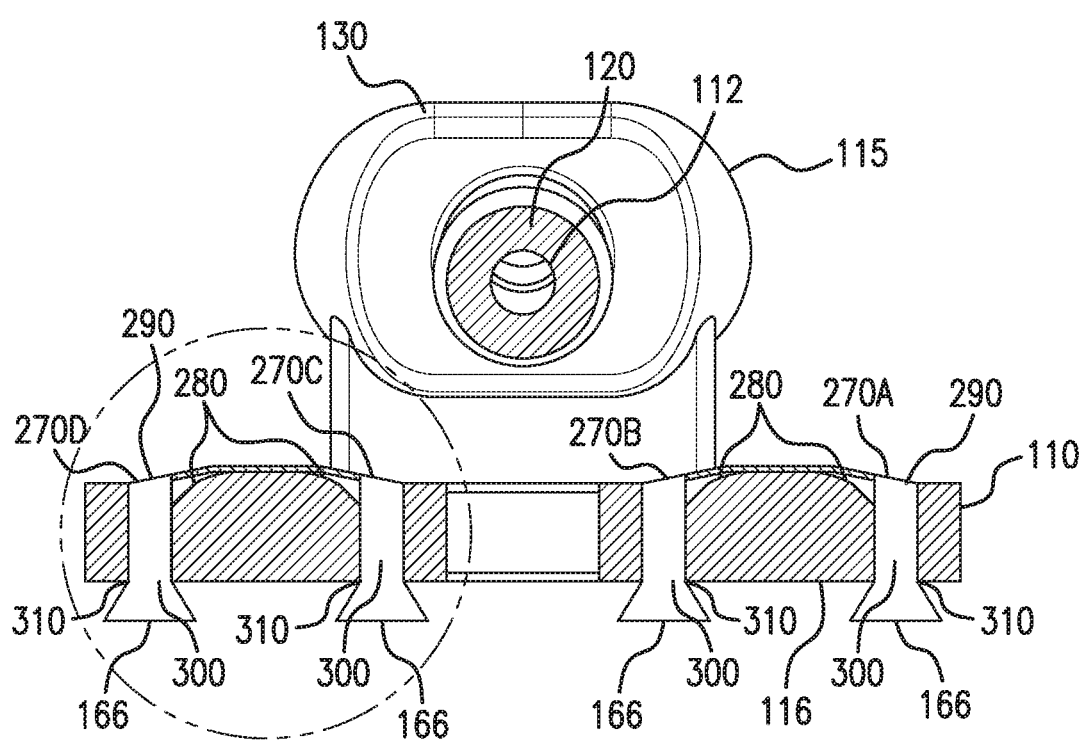

Although the embodiment shown and described above has a connecting portion 115 with a male luer connector 120 and a flow housing 130 other embodiments may have different configurations for the connecting portion 115. For example, as shown in FIGS. 6, 7, 8A and 8B, to allow the device/system 100 to connect to a tubing set 400, the system/device 100 may have a connecting portion 260 that includes two protrusions 250A/B that extend from a surface of the housing 110 and form a clasp 260 (e.g., a c-clamp). In such embodiments, the fluid line/tubing set 400 (which includes a section of tube 410 extending between a male luer connector 420 and a female luer connector 430) may be secured to the system/device 100 by pressing the male luer connector 420 into the clasp 260 such that at least one of the protrusions 250A/B flexes outward and snaps over the male luer connector 420 (FIG. 8B). Prior to establishing the connection to the tubing set 400, the user may connect the male luer connector 420 to the catheter in a manner similar to that described above.

Figure 6:
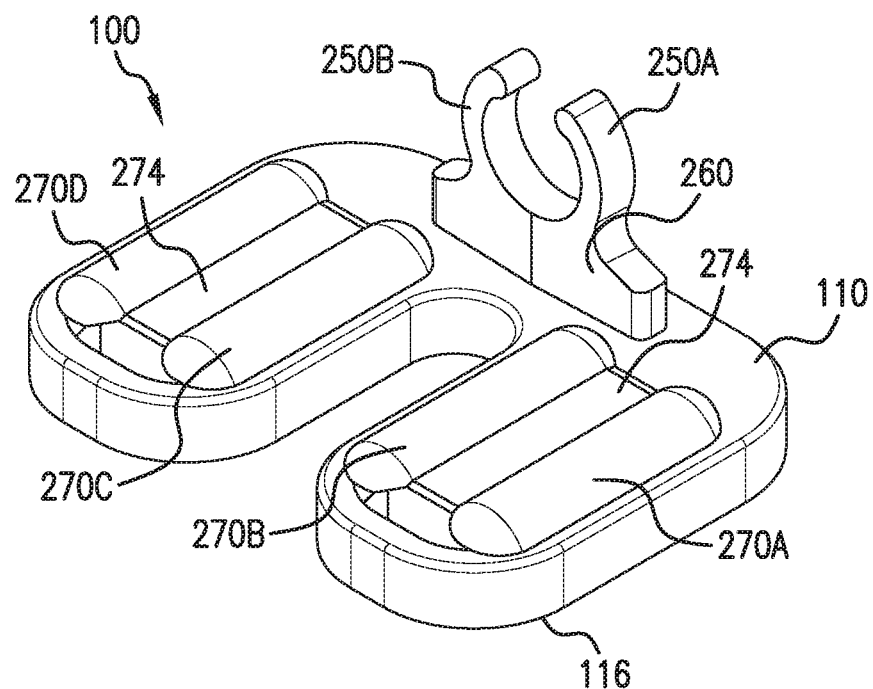
FIG. 6 schematically shows a perspective view of an alternative embodiment of a patient access site securement system in a pre-activated state, in accordance with some embodiments of the present invention.
Figure 7:
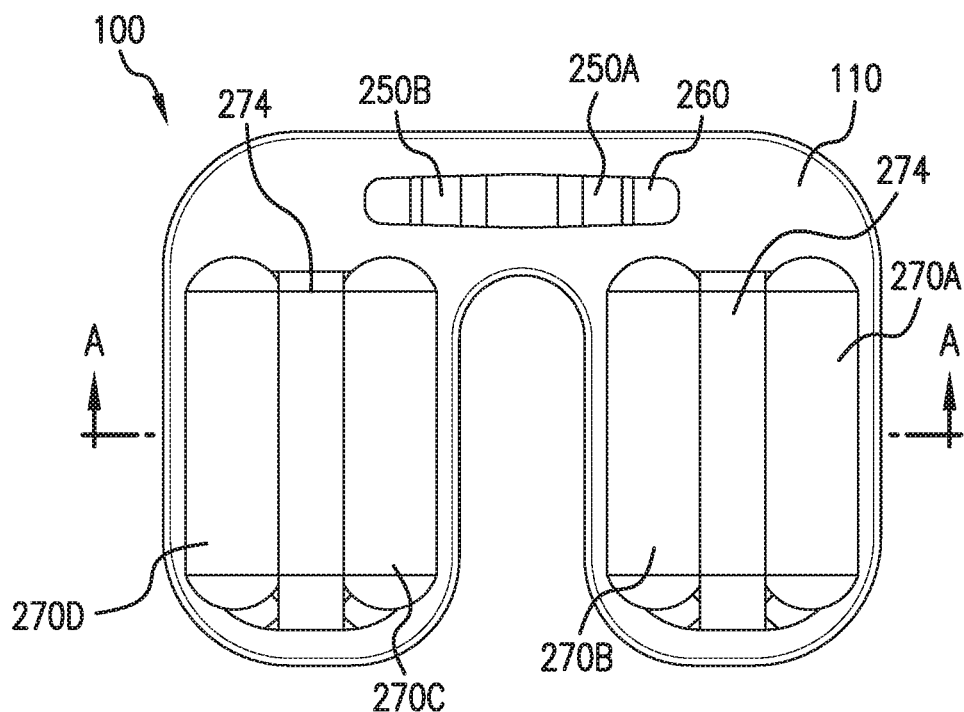
FIG. 7 schematically shows a top view of the patient access site securement system shown in FIG. 6, in accordance with various embodiments of the present invention.

Additionally, as also shown in FIG. 6, some embodiments may not have constant internal volume reservoirs. Rather, the reservoirs may be a series of pouches 270A-D that are attached to the housing 110. For example, two or more of the pouches (e.g., pouches 270A and 270B, and pouches 270C and 270D) may be connected with a connector 274 that may, in turn be attached to the housing 110 via RF welding, heat-staking, and/or adhesive, to name but a few ways. Alternatively, the pouches 270A-D may all be separate from one another and may be independently attached to the housing 110 or simply received such as in a well. The pouches 270A-D may be made in part from foil, flexible plastic, or other flexible material that allows at least a portion of the pouches 270A-D to be compressed by the user, reducing the internal volume to release the fluid 166.

During activation of the pouches 270A-D (e.g., to increase or decrease the level of securement of the system/device 100 as discussed above), the user may compress the pouch containing the appropriate/desired fluid 166 to cause the fluid 166 to be released from the pouch 270A-D. For example, the bottom of each pouch 270A-D may have a breachable portion 272A-D (e.g., scoring marks) on its underside that opens/breaches under the pressure applied by the user which, in turn, allows the fluid 166 to exit the pouch 270A-D (see FIGS. 10A/B and 11A/B) and enter the inlet 170A/B and flow through the internal fluid path 190A/B. This, in turn, will deflate the pouches 270A-D as shown in FIGS. 10A-10B, 11A-11B, and 16A-16C. Additionally or alternatively, as shown in FIGS. 12, and 13A-C, the housing 110 may include a number of cutting elements 280 located under the pouches 270A-D that cut into the underside of the pouches 270A-D as the user compresses them to access the interior and allow the fluid 166 to exit the pouches 270A-D. For example, the cutting elements 280 may be spikes, sharp edges, or similar sharp structures.

It should also be noted that, although the embodiment shown in FIGS. 1-5 and discussed above have a single inlet 170A/B for each reservoir 160A/B (e.g., located on the access element 220A/B), other embodiments may have multiple inlets 290 for each pouches 270A-D. Similarly, the system/device 100 may have multiple internal fluid paths 300 and multiple outlets 310. Therefore, once the fluid exits the pouches 270A-D, it may enter one of the inlets 290 (e.g., the one closest to where the fluid 166 exits the pouch 270A-D), flow through the internal fluid path 300 and exit one of the outlets 310 to interact with the contact surface 116 and/or the patient's skin. By having multiple inlets 290, internal fluid paths 290 and outlets 310, various embodiments may prevent fluid 166 from becoming trapped between the pouches 270A-D and the housing 110 and/or otherwise help to evenly distribute the fluid 166 on the contact surface 116 and/or patient's skin.

In a manner similar to the cap 210 described above, embodiments using pouches 270A-D may include a protective cover/shield 320 located over the pouches 270A-D that prevents the pouches 270A-D from accidentally being compressed and transitioning from the first/pre-activated state to the second/post-activated state (e.g., the deflated state shown in FIGS. 10A-10B, 11A-11B, and 16A-16D). It should be noted that FIGS. 12-17B show a housing 110 with a different connecting portion 115. For example, the connecting portion 115 shown in FIGS. 12-17B has a male luer connector 130 and a flow housing 130 like the embodiment shown in FIGS. 1-5. However, unlike the embodiment shown in FIGS. 1-5, the flow housing 130 does not rotate relative to the rest of the housing 110. Rather, the connecting portion 115 and the flow housing 130 essentially form a solid piece. To facilitate fluid flow though the housing 110 and into the catheter, the flow housing 120 has an inlet 154 located on the side of the flow housing 154 that may connect to a fluid line.

Figure 17A:
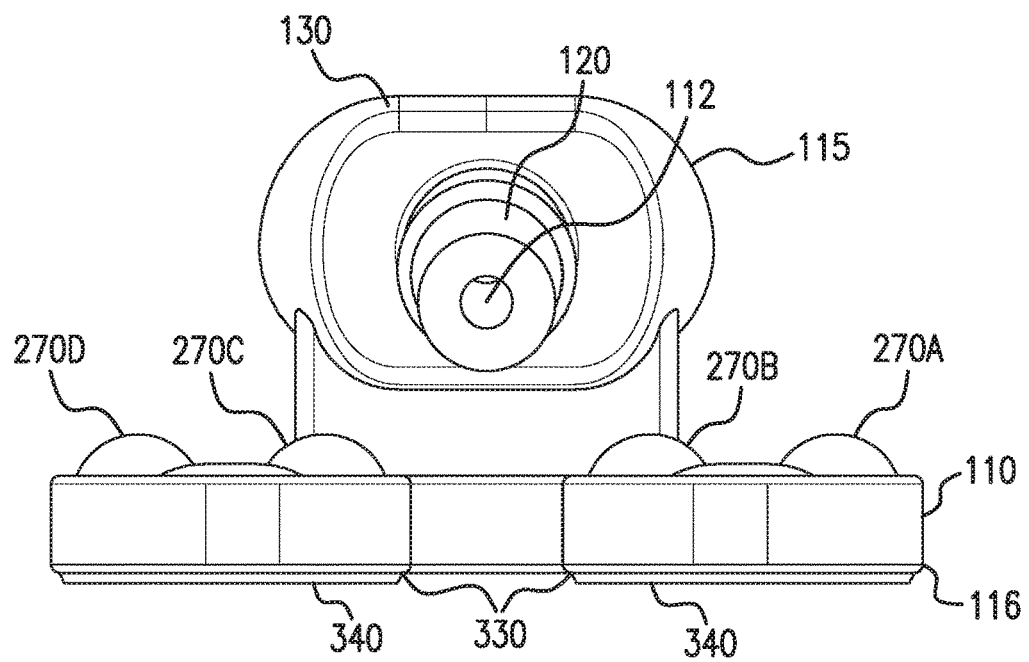
FIGS. 17A and 17B schematically show a front and bottom view of the patient access site securement system shown in FIG. 12 with an adhesive layer and release liner, in accordance with some embodiments of the present invention.
Figure 17B:
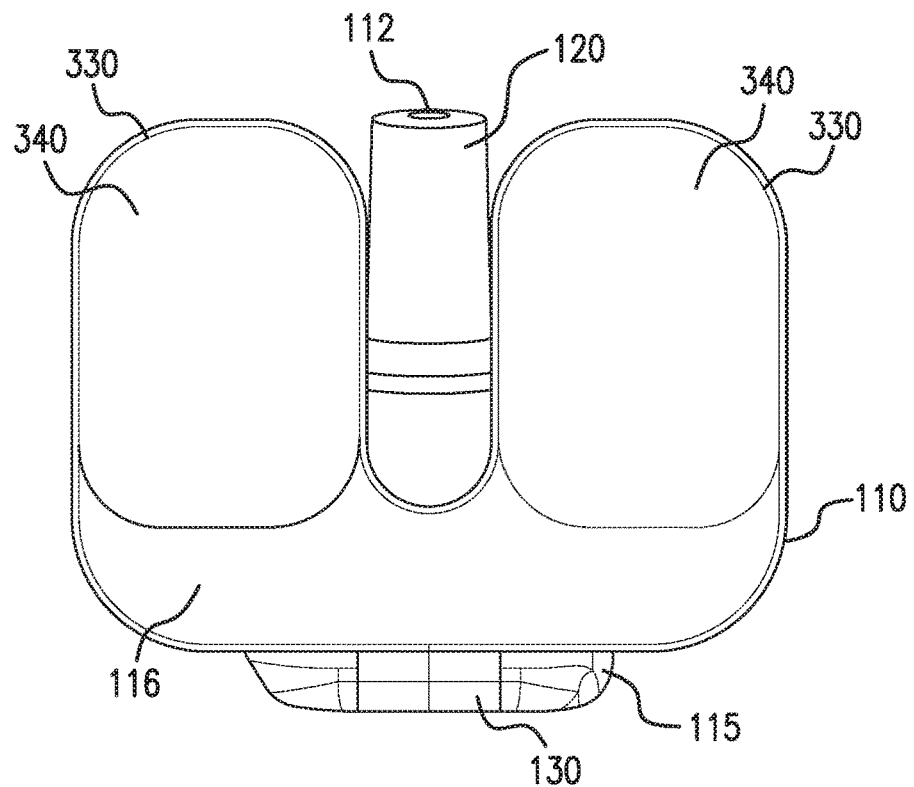

As discussed above, some embodiments may have a number of layers located under the contact surface 116, including an adhesive layer that may secure the system/device 100 to the patient. To that end, and as shown in FIGS. 17A and 17B, the underside of the housing 110 (e.g., the contact surface 116) may include an adhesive layer 330 that secures the housing 110 and the device 100 to the patient. Additionally, to prevent the adhesive layer 330 from accidentally sticking to something other than the patient prior to use, the device/system 100 may also include a release liner 340 that covers the adhesive layer 330 prior to use and may be removed to expose the adhesive layer 330 just prior to use.

In embodiments having an adhesive layer, it may not be necessary to have reservoirs (e.g., the constant internal volume reservoirs 160A/B or the pouches 270A-D) that contain adhesive. Rather, the reservoirs may contain the adhesive remover and/or the other possible fluids mentioned above. To that end, when the user wishes to remove the device/system 100 from the patient, they may transition the reservoir(s) from the first state to the second state (e.g., by pressing reservoirs 160A/B or compressing/deflating the pouches 270A-D) to release the adhesive remover, reduce the level of securement between the device 100 and patient, and make it easier to remove the device 100 from the patient.

It is important to note that size of the reservoirs (e.g., reservoirs 160A/B or the pouches 270A-D) may vary depending on the application and the type of fluid that each of the reservoirs contain. However, for embodiments containing adhesive and/or adhesive remover (e.g., to alter the level of securement), the reservoirs should contain at least enough fluid to fill the internal fluid path (e.g., fluid paths 190A/B and 300) through which the fluid flows. This will ensure that sufficient fluid interacts with the contact surface 116 and/or patient to alter the level of securement.

In some embodiments the reservoirs 160A/B and/or the pouches 270A-D may be removable and replaceable to allow the user to add additional fluid as needed after dispensing the fluid from a first reservoir/pouch or a first set of reservoirs/pouches. For example, if the both reservoirs 160A/B or all of the pouches 270A-D contain adhesive, the user may dispense the adhesive as discussed above and then replace one or more of the reservoirs 160A/B or pouches 270A-D with reservoirs/pouches containing the adhesive remover. Alternatively, the user may replace one or more of the reservoirs/pouches with a different fluid such as an antiseptic, skin protectant, or cleaning fluid. This provides the system/device 100 with flexibility to add and replace reservoirs/pouches as necessary to provide the user with the desired type of fluid.

It should also be noted that in some applications it may be beneficial for the system/device 100 to dispense/disperse the fluid beyond the contact surface 116 and the area just under the system/device 100. To that end, in some embodiments, one or more of the outlets 180A/B/310 may be located on the front side or back side of the device to allow the fluid 166 to disperse to the front or rear of the system/device 100. This allows the system/device 100 to disperse, for example, toward the catheter insertion site and create a microbial barrier over the insertion site. This, in turn, may alleviate the need for conventional dressings over the insertion site.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A patient access site securement system for securing a catheter and/or a fluid line attached to the catheter to a patient comprising:
    a housing having a first inlet, a first outlet and an internal fluid path between the first inlet and the first outlet, the housing also having a connecting portion configured to connect to the catheter and/or the fluid line attached to the catheter;
    a contact surface located on an underside of the housing and configured to position the patient access site securement system on the patient; and
    a first reservoir having an interior configured to hold a first liquid, the first reservoir configured to transition from a first state to a second state, the interior being in fluid communication with the first inlet when the first reservoir is in the second state to allow the first liquid to flow from the first inlet, through the internal fluid path and exit the first outlet such that the first liquid interacts with the contact surface and/or the patient to alter a level of securement between the catheter and/or the fluid line attached to the catheter and the patient,
    wherein the housing includes at least one access element configured to breach at least a portion of the first reservoir when transitioning towards the second state, thereby allowing the first liquid to flow into the first inlet.

2. The patient access site securement system according to claim 1, wherein the first liquid is an adhesive configured to increase the level of securement between the catheter and/or the fluid line attached to the catheter and the patient after interacting with the contact surface and/or the patient.

3. The patient access site securement system according to claim 1, wherein the first liquid is an adhesive remover configured to decrease the level of securement between the catheter and/or the fluid line attached to the catheter and the patient after interacting with the contact surface and/or the patient.

4. The patient access site securement system according to claim 1, wherein at least a portion of the first reservoir is configured to move relative to the first inlet from a first position to a second position to transition the first reservoir from the first state to the second state.

5. The patient access site securement system according to claim 1, wherein the housing includes a second inlet, a second outlet and a second internal fluid path between the second inlet and second outlet.

6. The patient access site securement system according to claim 5, further comprising a second reservoir having a second reservoir interior configured to hold a second liquid, the second reservoir configured to transition from a first state to a second state, the second reservoir interior being in fluid communication with the second inlet when the second reservoir is in the second state to allow the second liquid to flow from the second inlet, through the second internal fluid path and exit the second outlet such that the second liquid interacts with the contact surface, the first liquid, and/or patient to alter a level of securement between the catheter and the patient.

7. The patient access site securement system according to claim 1, wherein the first reservoir includes a breachable portion, the at least one access element configured to breach the breachable portion.

8. The patient access site securement system according to claim 1, wherein the access element is configured to at least partially enter the interior of the first reservoir when in the second state, thereby displacing at least a portion of the first liquid within the interior.

9. The patient access site securement system according to claim 1, wherein the access element is a cutting element.

10. The patient access site securement system according to claim 1, wherein the first reservoir is configured to be removed from the patient access site securement system.

11. The patient access site securement system according to claim 1, wherein at least a portion of the first liquid interacts with a catheter insertion site after exiting the first outlet.

12. The patient access site securement system according to claim 1, wherein the contact surface includes an adhering layer configured to secure the patient access site securement system to the patient.

13. The patient access site securement system according to claim 1, wherein the contact surface includes at least one fluid channel and/or at least one wicking member configured to facilitate fluid dispersion from the first outlet.

14. The patient access site securement system according to claim 1, wherein a volume within the first reservoir is reduced as the first reservoir is transitioned from the first state to the second state.

15. The patient access site securement system according to claim 1, further comprising a protective cap configured to be removeably secured to the patient access site securement system and cover at least a portion of the first reservoir, the protective cap preventing the first reservoir from transitioning from the first state to the second state when attached to the patient access site securement system.

16. The patient access site securement system according to claim 1, wherein the connecting portion includes at least a first protrusion extending from a surface of the housing, the at least first protrusion configured to receive and secure the catheter and/or fluid line.

17. The patient access site securement system according to claim 16, wherein the at least first protrusion flexes to receive and secure the catheter and/or fluid line.

18. A method for securing a catheter and/or a fluid line attached to the catheter to a patient comprising:
providing a patient access site securement system, the patient access site securement system including:
a housing having a first inlet, a first outlet and an internal fluid path between the first inlet and the first outlet, the housing also having a connecting portion configured to connect to the catheter and/or the fluid line attached to the catheter,
a contact surface located on an underside of the housing and configured to position the patient access site securement system on the patient, and
a first reservoir having an interior configured to hold a first liquid, the first reservoir configured to transition from a first state to a second state, the interior being in fluid communication with the first inlet when the first reservoir is in the second state to allow the first liquid to flow from the first inlet, through the internal fluid path and exit the first outlet; connecting a catheter and/or a fluid line to the connecting portion of the housing; positioning the contact surface on the patient;
transitioning the first reservoir from the first state to the second state, thereby causing the first liquid to interact with the contact surface and/or the patient and alter a level of securement between the catheter and/or the fluid line attached to the catheter and the patient,
wherein the housing includes at least one access element configured to breach at least a portion of the first reservoir when transitioning towards the second state, thereby allowing the first liquid to flow into the first inlet.

19. The method according to claim 18, wherein the first liquid is an adhesive configured to increase the level of securement between the catheter and/or the fluid line attached to the catheter and the patient after interacting with the contact surface and/or the patient.

20. The method according to claim 18, wherein the first liquid is an adhesive remover configured to decrease the level of securement between the catheter and/or the fluid line attached to the catheter and the patient after interacting with the contact surface and/or the patient.

21. The method according to claim 18, wherein transitioning the first reservoir from the first state to the second state includes moving at least a portion of the first reservoir relative to the first inlet from a first position to a second position.

22. The method according to claim 18, wherein the housing includes a second inlet, a second outlet and a second internal fluid path between the second inlet and second outlet.

23. The method according to claim 22, wherein the patient access site securement system further includes a second reservoir having a second reservoir interior configured to hold a second liquid, the method further comprising:

transitioning the second reservoir from a first state to a second state, the second reservoir interior being in fluid communication with the second inlet when the second reservoir is in the second state to allow the second liquid to flow from the second inlet, through the second internal fluid path and exit the second outlet such that the second liquid interacts with the contact surface, the first liquid, and/or patient to alter a level of securement between the catheter and the patient.

24. The method according to claim 18, wherein the first reservoir includes a breachable portion, the at least one access element configured to breach the breachable portion.

25. A method according to claim 18, wherein the access element is configured to at least partially enter the interior of the first reservoir when in the second state, thereby displacing at least a portion of the first liquid within the interior.

26. The method according to claim 18, wherein the access element is a cutting element.

27. The method according to claim 18, wherein the first reservoir is configured to be removed from the patient access site securement system.

28. The method according to claim 18, wherein at least a portion of the first liquid interacts with a catheter insertion site after exiting the first outlet.

29. The method according to claim 18, wherein the contact surface includes an adhering layer configured to secure the patient access site securement system to the patient.

30. The method according to claim 18, wherein the contact surface includes at least one fluid channel and/or at least one wicking member configured to facilitate fluid dispersion from the first outlet.

31. The method according to claim 18, wherein transitioning the first reservoir from the first state to the second state causes a volume within the first reservoir to be reduced.

32. The method according to claim 18, wherein the patient access site securement system further includes a protective cap configured to be removeably secured to the patient access site securement system and cover at least a portion of the first reservoir, the protective cap preventing the first reservoir from transitioning from the first state to the second state when attached to the patient access site securement system.

33. The method according to claim 18, wherein the connecting portion includes at least a first protrusion extending from a surface of the housing, the at least first protrusion configured to receive and secure the catheter and/or fluid line.

34. The method according to claim 33, wherein the at least first protrusion flexes to receive and secure the catheter and/or fluid line.

* * * * *